(12) United States Patent
Imperiali et al.

(10) Patent No.: US 7,442,529 B2
(45) Date of Patent: Oct. 28, 2008

(54) FLUORESCENT PROBES FOR BIOLOGICAL STUDIES

(75) Inventors: Barbara Imperiali, Cambridge, MA (US); Eugenio Vazquez, Santiago de Compostela (ES)

(73) Assignee: Massachusetts Institute of Technology, Cambridge, MA (US)

( * ) Notice: Subject to any disclaimer, the term of this patent is extended or adjusted under 35 U.S.C. 154(b) by 142 days.

(21) Appl. No.: 11/106,349

(22) Filed: Apr. 13, 2005

(65) Prior Publication Data

US 2006/0234206 A1  Oct. 19, 2006

(51) Int. Cl.
*C12P 13/04* (2006.01)

(52) U.S. Cl. .................. 435/106; 536/26.6

(58) Field of Classification Search .......... None
See application file for complete search history.

(56) References Cited

U.S. PATENT DOCUMENTS 5,854,275 A * 12/1998 Robinson .................. 514/411

OTHER PUBLICATIONS

Brown, et al., J. Med. Chem. 1994, 37, 674-688.*
Brown, 1994, J. Med. Chem., 37, 674-688.*
M. Eugenio Vazquez et al., "Photophysics and Biological Applications of the Environment-Sensitive Fluorophore 6-*N,N*-Dimethylamino-2,3-Naphthalimide" (and Supporting Information), *J. Am. Chem. Soc.* 2005, vol. 127, No. 4, 1300-1306.
Gregorio Weber et al., "Synthesis and Spectral Properties of a Hydrophobic Fluorescent Probe: 6-Propionyl-2-(dimethylamino)naphthalene", *Biochemistry*, vol. 18, No. 14, 3075-3078, 1979.
Bruce E. Cohen et al., "Probing Protein Electrostatics With a Synthetic Fluorescent Amino Acid", *Science*, vol. 296, 1700-1703, May 31, 2002.
Ivo Grabchev et al., "Synthesis and Properties of Fluorescent 1,8-Naphthalimide Dyes for Application in Liquid Crystal Displays", *J. Mater. Chem.*, 2000, 10, 1291-1296, Nov. 19, 1999.
F. Cacialli et al., "Naphthalimide Side-Chain Polymers for Organic Light-Emitting Diodes: Band-Offset Engineering and Role of Polymer Thickness", *J. Appl. Phys.*, vol. 83, No. 4, 2343-2356, Feb. 15, 1998.
Barluenga, J. et al., "Easy and Regioselective Synthesis of Highly functionalized o-Quinodimethide Precursors from Fischer Carbene Complexes and Isocyanides," *Chem. Eur. J.*, 2002, pp. 4149-4163.
Lee, H. et al., "Synthesis of 2,3,8-Trisubstituted 7*H*-Isoindolo[5,6-g]Quinoxaline-5,7,9,11(8*H*)-tetraones," *Heterocycles*, vol. 63, No. 4, 2004, pp. 819-826.
Moder, K. et al., "Defined Dimensional Alterations in Enzyme Substrates. Synthesis and Enzymatic Evaluation of Some *lin*-Naphthopurines," *J. Am. Chem. Soc.*, 1982, 104, 2613-2624.
Pozarentzi, M. et al., "The first benzodiazpine *o*-quinodimethane: generation and Diels-Alder reactions," *Tetrahedron Letters*, 44 (2003) pp. 2007-2009.
Stevenson, T. et al., "Defined Dimensional Alterations in Enzyme Substrates. *lin*-Naphthloadenine and *lin*-Naphthoadenosine," *J. Org. Chem.*, 1984, 49, pp. 2158-2164.
Suzuki, T. et al., "Preparation and Crystal Structures of Tetracyanoquinodimethans Fused with [1,2,5]Selenadiazole Units," *Chemistry Letters*, 1987, pp. 2285-2288.

* cited by examiner

*Primary Examiner*—Andrew D. Kosar
*Assistant Examiner*—Satyanarayana Gudibande
(74) *Attorney, Agent, or Firm*—Wolf, Greenfield & Sacks, P.C.

(57) ABSTRACT

The present invention provides fluorescent compounds of formula (I)

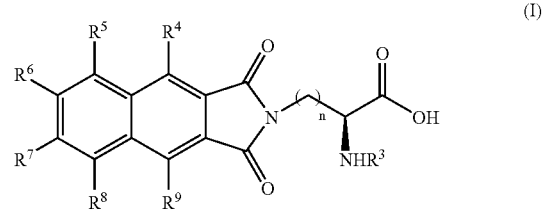

and methods monitoring protein-protein interactions.

4 Claims, 7 Drawing Sheets

US 7,442,529 B2

FLUORESCENT PROBES FOR BIOLOGICAL STUDIES

FEDERALLY SPONSORED RESEARCH OR DEVELOPMENT

The subject matter of this application was developed in part with funding from the Cell Migration Consortium (grant application no. GM64346) and National Science Foundation (grant application no. CHE-0414243). The government may have certain rights in this technology.

BACKGROUND

Fluorescence is the result of a three-stage process that occurs when certain molecules absorb energy. The three stages comprise: 1) excitation; 2) excited-state lifetime; and 3) fluorescence emission. During stage 1, excitation, a photon of a certain energy is absorbed by the fluorophore. The fluorophore is initially in its ground state ($S_0$). Absorption of the photon causes that fluorophore to become excited. The energy of the absorbed photon is transferred to an electron. The electron is transferred to a higher energy state. The fluorophore exists in an excited electronic singlet state ($S_{1'}$), also called an excited state. The excited state of the fluorophore exists for a finite time, typically $10^{-8}$ to $10^{-9}$ seconds. During the excited state, the fluorophore changes in its translational, vibrational, and electronic energy states, and is subject to interactions with its molecular environment. The excited fluorophore releases energy and returns to the ground state, $S_0$, by fluorescence emission. Other processes such as fluorescence energy transfer, intersystem crossing, and collisional quenching may also depopulate $S_1$. The ratio of the number of fluorescence photons emitted, during the emission stage, to the number of photons absorbed, during the excitation stage, is termed the quantum yield. The quantum yield is a measure of the efficiency of fluorescence in competition with other processes such as fluorescence energy transfer, intersystem crossing, and collisional quenching.

During the third stage, fluorescence emission, a photon of energy hv (where h is Planck's constant and v is the frequency of the photon) is emitted, returning the fluorophore to its ground state $S_0$. The energy of the emitted photon is lower than the energy of the photon absorbed during the excitation stage. The difference in energy can be attributed to dissipation through processes during the excited-state lifetime, such processes include fluorescence energy transfer, intersystem crossing, and collisional quenching. The difference in energy of the absorbed photon and the emitted photon is called the Stokes shift. The Stokes shift is fundamental to the sensitivity of fluorescence techniques because it allows emission photons to be detected against a low background, and at a different wavelength than the excitation photons.

Compounds that have fluorescent properties have numerous uses. Fluorescent molecules can be used in single molecule spectroscopy, liquid crystal displays, light emitting diodes, solar energy collectors, and laser active media. Fluorescent molecules whose spectra or quantum yields are sensitive to their environments are valuable as fluorescent dyes and in the study of heterogeneous media, organized media, and biological media.

The present invention provides compounds that can be used to monitor biological interactions continuously with a fluorescence readout. The compounds of the present invention are environment-sensitive fluorophores which have spectroscopic behavior that is dependent on the physicochemical properties of the surrounding environment. The compounds of the present invention can be used in biochemical research to monitor ions, small molecules, and biological processes such as protein folding, protein-protein interactions and phosphorylation events.

Environment-sensitive fluorophores are a special class of chromophores that have spectroscopic behavior that is dependent on the physicochemical properties of the surrounding environment. Solvatochromic fluorophores display sensitivity to the polarity of the local environment. These molecules exhibit a low quantum yield in aqueous solution, but become highly fluorescent in nonpolar solvents or when bound to hydrophobic sites in proteins or membranes. Examples of solvatochromic fluorophores include 2-propionyl-6-dimethylaminonaphthalene (PRODAN) (Weber et al. *Biochemistry* 1979, 18, 3075-3078; Cohen et al. *Science* 2002, 296, 1700-1703), 4-dimethylamino phthalimide (4-DMAP) (Saroja et al. *J. Fluoresc.* 1998, 8, 405-410), and 4-amino-1,8-naphthalimide derivatives (Grabchev et al. *J. Photochem. Photobiol., A* 2003, 158, 37-43; Martin et al. *J. Lumin.* 1996, 68, 157-146). Although PRODAN and derivatives are widely used, these probes have limitations resulting from the relatively intense fluorescence even in aqueous environments. Thus, there is a need for alternate compounds.

BRIEF SUMMARY

The present invention provides novel compounds of the formula (I):

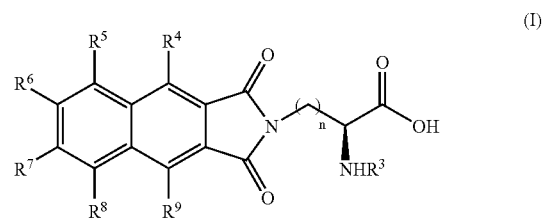

where n, $R^3$, $R^4$, $R^5$, $R^6$, $R^7$, $R^8$ and $R^9$ are as defined below. One especially preferred compound (III) referred to as Dap (6DMN) is disclosed.

The present invention also provides peptides containing the compound (I) of the present invention.

The present invention also provides a method for probing biological interactions using peptides containing the compound (I).

DETAILED DESCRIPTION OF THE INVENTION

General

Figure 1:
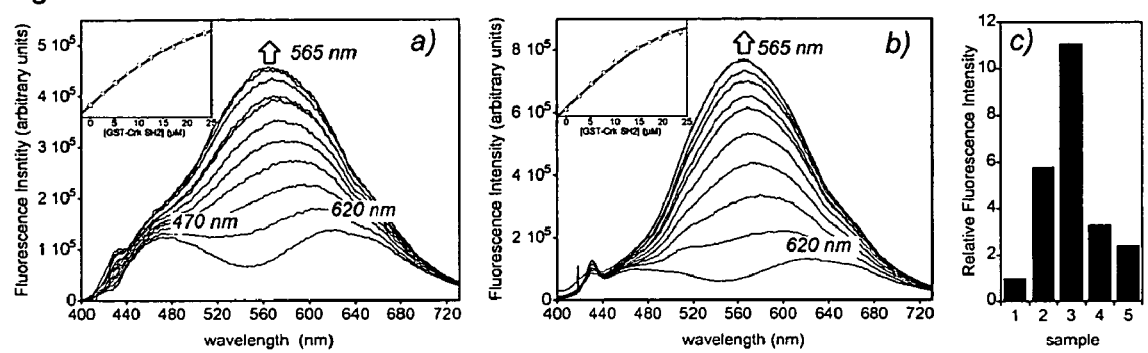
FIG. 1 are fluorescence titrations of peptides (Crk-bp and Crk-bp2) binding to GST-Crk SH2 domain. (a) Peptide Crk-bp (20 μM in PBS buffer, pH 7.5) with GST-Crk SH2, and (b) Peptide Crk-bp2 (20 μM in PBS buffer, pH 7.5) with GST-Crk SH2. Inserts show plots of the fluorescence emission intensity with the best fitting binding curves. Spectra were corrected for the dilution upon addition of the protein solution. (c) Relative fluorescence emission intensities at 565 nm for: 1) Peptides Crk-bp and Crk-bp2 in buffer. 2) Peptide Crk-bp saturated with GST-Crk SH2. 3) Peptide Crk-bp2 saturated with GST-Crk SH2. 4) Peptide Crk-bp2 saturated with GST-Abl SH2. 5) Peptide Crk-bp2 saturated with GST-PI3K SH2.

The present invention is directed to compounds and salts thereof, compositions and methods useful in monitoring biological interactions continuously with a fluorescence readout.

Abbreviations and Definitions

When describing the compounds, compositions, methods and processes of this invention, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, thioalkyl, aminoalkyl, and the like.

"Alkoxy" refers to —O-alkyl. Examples of an alkoxy group include methoxy, ethoxy, n-propoxy, etc.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Aryl" refers to a polyunsaturated, aromatic hydrocarbon group having a single ring (monocyclic) or multiple rings (bicyclic), which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups can be substituted or unsubstituted, unless otherwise indicated.

"Fluorescence" encompasses the release of fluorescent energy. Less broadly, the term "fluorescence" refers to fluorescent emission, the rate of change of fluorescence over time (i.e., fluorescence lifetime), fluorescence polarization, fluorescence anisotropy, and fluorescence resonance energy transfer. See Eftink, M. R., *Biophysical J.* 66:482-501 (1994).

"Fluorescence probe molecule" refers to a compound of the present invention. The compound, after excitement by light of a defined wavelength or defined range of wavelengths, is capable of emitting fluorescent energy. The fluorescent molecule or a compound may be capable of binding to a peptide, protein, membrane or receptor.

"Halo" or "halogen", by itself or as part of a substituent refers to a chlorine, bromine, iodine, or fluorine atom.

"Haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic ring containing at least one heteroatom (typically 1 to 5 heteroatoms) selected from nitrogen, oxygen or sulfur. The heterocyclyl ring may be monocyclic or bicyclic. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

In one preferred embodiment, heterocyclic groups may be represented by formula (AA) below:

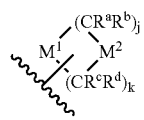

AA where formula (AA) is attached via a free valence on either $M^1$ or $M^2$; $M^1$ represents O, $NR^e$, or $S(O)_l$; $M^2$ represents $CR^fR^g$, O, $S(O)_l$, or $NR^e$; l is 0, 1 or 2; j is 1, 2 or 3 and k is 1, 2 or 3, with the proviso that j+k is 3, 4, or 5; and $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, $-COR^h$, $-CO_2R^h$, $-CONR^hR^i$, $-NR^hCOR^i$, $-SO_2R^h$, $-SO_2NR^hR^i$, $-NSO_2R^hR^i$, $-NR^hR^i$, $-OR^h$, $-Q^1COR^h$, $-Q^1CO_2R^h$, $-Q^1CONR^hR^i$, $-Q^1NR^hCOR^i$, $-Q^1SO_2R^{28}$, $-Q^1SO_2NR^hR^i$, $-Q^1NSO_2R^hR^i$, $-Q^1NR^hR^i$, $-Q^1OR^h$, wherein $Q^1$ is a member selected from the group consisting of $C_{1-4}$ alkylene, $C_{2-4}$ alkenylene and $C_{2-4}$ alkynylene, and $R^h$ and $R^i$ are independently selected from the group consisting of hydrogen and $C_{1-8}$ alkyl, and wherein the aliphatic portions of each of the $R^a$, $R^b$, $R^c$, $R^d$, $R^e$, $R^f$, $R^g$, $R^h$ and $R^i$ substituents are optionally substituted with from one to three members selected from the group consisting of halogen, $-OH$, $-OR''$, $-OC(O)NHR''$, $-OC(O)NR''R^o$, $-SH$, $-SR''$, $-S(O)R''$, $-S(O)_2R''$, $-SO_2NH_2$, $-S(O)_2NHR''$, $-S(O)_2NR''R^o$, $-NHS(O)_2R''$, $-NR''S(O)_2R^o$, $-C(O)NH_2$, $-C(O)NHR''$, $-C(O)NR''R^o$, $-C(O)R''$, $-NHC(O)R''$, $-NR''C(O)R^o$, $-NHC(O)NH_2$, $-NR''C(O)NH_2$, $-NR''C(O)NHR^o$, $-NHC(O)NHR''$, $-NR''C(O)NR^oR^p$, $-NHC(O)NR''R^o$, $-CO_2H$, $-CO_2R''$, $-NHCO_2R''$, $-NR''CO_2R^o$, $-CN$, $-NO_2$, $-NH_2$, $-NHR''$, $-NR''R^o$, $-NR''S(O)NH_2$ and $-NR''S(O)_2NHR^o$, wherein $R''$, $R^o$ and $R^p$ are independently an unsubstituted $C_{1-8}$ alkyl. Additionally, any two of $R^a$, $R^b$, $R^c$, $R^d$, $R^e$, $R^f$ and $R^g$ may be combined to form a bridged or spirocyclic ring system.

In one preferred embodiment, the number of $R^a+R^b+R^c+R^d$ groups that are other than hydrogen is 0, 1 or 2. In a more preferred embodiment, $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, $-COR^h$, $-CO_2R^h$, $-CONR^hR^i$, $-NR^hCOR^i$, $-SO_2R^h$, $-SO_2NR^hR^i$, $-NSO_2R^hR^i$, $-NR^hR^i$, and $-OR^h$, wherein $R^h$ and $R^i$ are independently selected from the group consisting of hydrogen and unsubstituted $C_{1-8}$ alkyl and wherein the aliphatic portions of each of the $R^a$, $R^b$, $R^c$, $R^d$, $R^e$, $R^f$ and $R^g$ substituents are optionally substituted with from one to three members selected from the group consisting of halogen, $-OH$, $-OR''$, $-OC(O)NHR''$, $-OC(O)NR''R^o$, $-SH$, $-SR''$, $-S(O)R''$, $-S(O)_2R''$, $-SO_2NH_2$, $-S(O)_2NHR''$, $-S(O)_2NR''R^o$, $-NHS(O)_2R''$, $-NR''S(O)_2R^o$, $-C(O)NH_2$, $-C(O)NHR''$, $-C(O)NR''R^o$, $-C(O)R''$, $-NHC(O)R''$, $-NR''C(O)R^o$, $-NHC(O)NH_2$, $-NR''C(O)NH_2$, $-NR''C(O)NHR^o$, $-NHC(O)NHR''$, $-NR''C(O)NR^oR^p$, $-NHC(O)NR''R^o$, $-CO_2H$, $-CO_2R''$, $-NHCO_2R''$, $-NR''CO_2R^o$, $-CN$, $-NO_2$, $-NH_2$, $-NHR''$, $-NR''R^o$, $-NR''S(O)NH_2$ and $-NR''S(O)_2NHR^o$, wherein $R''$, $R^o$ and $R^p$ are independently an unsubstituted $C_{1-8}$ alkyl.

In a more preferred embodiment, $R^a$, $R^b$, $R^c$, $R^d$, $R^e$, $R^f$, and $R^g$ are independently hydrogen or $C_{1-4}$ alkyl. In another preferred embodiment, at least three of $R^a$, $R^b$, $R^c$, $R^d$, $R^e$, $R^f$, and $R^g$ are hydrogen.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is oxo ($=O$ or $-O^-$), the resulting group may have either a carbonyl ($-C(O)-$) or a N-oxide ($-N^+-O^-$).

Suitable substituents for substituted alkyl include halogen, $-CN$, $-CO_2R'$, $-C(O)R'$, $-C(O)NR'R''$, oxo ($=O$ or $-O^-$), $-OR'$, $-OC(O)R'$, $-OC(O)NR'R',$' $-NO_2$, $-NR'C(O)R''$, $-NR'''C(O)NR'R''$, $-NR'R''$, $-NR'CO_2R''$, $-NR'S(O)R''$, $-NR'S(O)_2R'''$, $-NR'''S(O)NR'R''$, $-NR'''S(O)_2NR'R''$, $-SR'$, $-S(O)R'$, $-S(O)_2R'$, $-S(O)_2NR'R''$, $-NR'-C(NHR'')=NR'''$, $-SiR'R''R'''$, $-N_3$, substituted or unsubstituted $C_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical.

Suitable substituents for substituted ring include halogen, —CN, —CO$_2$R', —C(O)R', —C(O)NR'R", oxo (=O or —O⁻), —OR', —OC(O)R', —OC(O)NR'R", —NO$_2$, —NR'C(O)R", —NR'''C(O)NR'R", —NR'R", —NR'CO$_2$R", —NR'S(O)R", —NR'S(O)$_2$R", —NR'''S(O)NR'R", —NR'''S(O)$_2$NR'R", —SR', —S(O)R', —S(O)$_2$R', —S(O)$_2$NR'R", —NR'—C(NHR")=NR''', —SiR'R"R''', —N$_3$, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10 membered heterocyclyl. The number of possible substituents range from zero to the total number of open valences on the ring system.

As used above, R', R" and R''' each independently refer to a variety of groups including hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R''', or R' and R''' may together with the atom(s) to which they are attached, form a substituted or unsubstituted 5-, 6- or 7-membered ring.

"Heteroatom" is meant to include oxygen (O), nitrogen (N), sulfur (S) and silicon (Si).

"N-protecting group" refers to an easily removable group which is known in the art to protect an amino group against undesirable reaction during synthetic procedures and to be selectively removable. The use of N-protecting groups is well known in the art for protecting groups against undesirable reactions during a synthetic procedure and many such protecting groups are known. Commonly used N-protecting groups are known to those skilled in the art, examples of which are disclosed in Greene and Wuts, *Protective Groups in Organic Synthesis,* 2nd ed.; John Wiley & Sons, New York, 1991). Examples of N-protecting groups include, but are not limited to, acyl groups including formyl, acetyl (Ac), trifluoroacetyl, trichloroacetyl, propionyl, pivaloyl, t-butylacetyl, acylisothiocyanate, aminocaproyl, benzoyl and the like; acyloxy groups, including t-butyloxycarbonyl (Boc), benzyloxycarbonyl (Cbz), 9-fluorenylmethoxycarbonyl (Fmoc), p-methoxybenzyloxycarbonyl, methoxycarbonyl, ethoxycarbonyl, allyloxycarbonyl and the like; sulfonyl groups such as benzenesulfonyl, p-toluenesulfonyl and the like; arylalkyl groups such as benzyl, triphenylmethyl, benzyloxymethyl and the like; and silyl groups such as trimethylsilyl, t-butyidimethylsilyl and the like.

All of the above terms (e.g., "alkyl," "aryl," "heteroaryl" etc.), in some embodiments, include both substituted and unsubstituted forms of the indicated groups. These groups may be substituted 1 to 10 times, as chemically allowed. Suitable substituents include alkyl, aryl, heteroaryl, heterocyclyl, halogen, alkoxy, oxygen, and nitrogen.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "biological interactions" encompasses the interaction of a compound or molecule with a target molecule.

"Protein" and "peptide", as used herein, are synonymous. For proteins or peptides, the term "unfolding" encompasses any change in structure due to heating. For example, the term "unfolding" refers to the transition of from the liquid crystalline state to the molten globule state. In the molten globule state, tertiary and quaternary structure has been altered, relative to the native state of the protein, and at least some secondary structure remains intact. The term "unfolding" also encompasses loss of crystalline ordering of amino acid sidechains, secondary, tertiary or quaternary structure. The term "unfolding" also encompasses formation of a random coil.

"Folding" and "refolding," and "renaturing" refer to the acquisition of the correct amino acid side-chain ordering, secondary, tertiary, or quaternary structure, of a protein or a nucleic acid, which affords the full chemical and biological function of the biomolecule.

The term "target molecule" encompasses peptides, proteins, nucleic acids, ions, and other receptors. The term encompasses both enzymes, and proteins which are not enzymes. The term encompasses monomeric and multimeric proteins. Multimeric proteins may be homomeric or heteromeric. The term encompasses nucleic acids comprising at least two nucleotides, such as oligonucleotides. Nucleic acids can be single-stranded, double-stranded, or triple-stranded. The term encompasses a nucleic acid which is a synthetic oligonucleotide, a portion of a recombinant DNA molecule, or a portion of chromosomal DNA. The term target molecule also encompasses portions of peptides, proteins, and other receptors which are capable of acquiring secondary, tertiary, or quaternary structure through folding, coiling or twisting. The target molecule may be substituted with substituents including, but not limited to, cofactors, coenzymes, prosthetic groups, lipids, oligosaccharides, or phosphate groups.

The terms "target molecule" and "receptor" are synonymous.

Examples of target molecules are included, but not limited to those disclosed in Faisst, S. et al., *Nucleic Acids Research* 20:3-26 (1992); Pimentel, E., *Handbook of Growth Factors*, Volumes I-III, CRC Press, (1994); Gilman, A. G. et al., *The Pharmacological Basis of Therapeutics*, Pergamon Press (1990); Lewin, B., *Genes V*, Oxford University Press (1994); Roitt, I., *Essential Immunology*, Blackwell Scientific Publ. (1994); Shimizu, Y., *Lymphocyte Adhesion Molecules*, R G Landes (1993); Hyams, J. S. et al., *Microtubules*, Wiley-Liss (1995); Montreuil, J. et al., *Glycoproteins*, Elsevier (1995); Woolley, P., *Lipases: Their Structure Biochemistry and Applications*, Cambridge University Press (1994); Kurjan, J., *Sig-* nal Transduction: Prokaryotic and Simple Eukaryotic Systems, Academic Press (1993); Kreis, T., et al., Guide Book to the Extra Cellular Matrix and Adhesion Proteins, Oxford University Press (1993); Schlesinger, M. J., Lipid Modifications of Proteins, CRC Press (1992); Conn, P. M., Receptors: Model Systems and Specific Receptors, Oxford University Press (1993); Lauffenberger, D. A. et al, Receptors. Models For Binding Trafficking and Signaling, Oxford University Press (1993); Webb, E. C., Enzyme Nomenclature, Academic Press (1992); Parker, M. G., Nuclear Hormone Receptors; Molecular Mechanisms, Cellular Functions Clinical Abnormalities, Academic Press Ltd. (1991); Woodgett, J. R., Protein Kinases, Oxford University Press (1995); Balch, W. E. et al., Methods in Enzymology, Vol. 257, Pt. C: "Small GTPases and Their Regulators: Proteins Involved in Transport," Academic Press (1995); The Chaperonins, Academic Press (1996); Pelech, L., Protein Kinase Circuitry in Cell Cycle Control, R G Landes (1996); Atkinson, Regulatory Proteins of the Complement System, Franklin Press (1992); Cooke, D. T. et al., Transport and Receptor Proteins of Plant Membranes: Molecular Structure and Function, Plenum Press (1992); Schumaker, V. N., Advances in Protein Chemistry: Lipoproteins, Apolipoproteins, and Lipases, Academic Press (1994); Brann, M., Molecular Biology of G-Protein-Coupled Receptors: Applications of Molecular Genetics to Pharmacology, Birkhauser (1992); Konig, W., Peptide and Protein Hormones: Structure, Regulations, Activity—A Reference Manual, VCH Publ. (1992); Tuboi, S. et al., Post-Translational Modification of Proteins, CRC Press (1992); Heilmeyer, L. M., Cellular Regulation by Protein Phosphorylation, Springer-Verlag (1991); Takada, Y., Integrin: The Biological Problem, CRC Press (1994); Ludlow, J. W., Tumor Suppressors: Involvement in Human Disease, Viral Protein Interactions, and Growth Regulation, R G Landes (1994); Schlesinger, M. J., Lipid Modification of Proteins, CRC Press (1992); Nitsch, R. M., Alzheimer's Disease. Amyloid Precursor Proteins, Signal Transduction, and Neuronal Transplantation, New York Academy of Sciences (1993); Cochrane, C. G., et al., Cellular and Molecular Mechanisms of Inflammation, Vol. 3: Signal Transduction in Inflammatory Cells, Part A, Academic Press (1992); Gupta, S. et al., Mechanisms of Lymphocyte Activation and Immune Regulation IV: Cellular Communications, Plenum Press (1992); Authi, K. S. et al., Mechanisms of Platelet Activation and Control, Plenum Press (1994); Grunicke, H., Signal Transduction Mechanisms in Cancer, R G Landes (1995); Latchman, D. S., Eukaryotic Transcription Factors, Academic Press (1995).

The term "contacting a target molecule" refers broadly to placing the target molecule in solution with the molecule to be screened for binding or with the condition(s) to be tested for stabilizing the target molecule. Less broadly, contacting refers to the turning, swirling, shaking or vibrating of a solution of the target molecule and the molecule to be screened for binding. More specifically, contacting refers to the mixing of the target molecule with the molecule to be tested for binding. Mixing can be accomplished, for example, by repeated uptake and discharge through a pipette tip, either manually or using an automated pipetting device. Preferably, contacting refers to the equilibration of binding between the target molecule and the molecule to be tested for binding. Contacting can occur in the container, infra, or before the target molecule and the molecule to be screened are placed in the container.

The target molecule may be contacted with a nucleic acid prior to being contacted with the molecule to be screened for binding. The target molecule may be complexed with a peptide prior to being contacted with the molecule to be screened for binding. The target molecule may be phosphorylated or dephosphorylated prior to being contacted with the molecule to be screened for binding.

A carbohydrate moiety may be added to the target molecule before the target molecule is contacted with the molecule to be screened for binding. Alternatively, a carbohydrate moiety may be removed from the target molecule before the target molecule is contacted with the molecule to be screened for binding.

The term "container" refers to any vessel or chamber in which the receptor and molecule to be tested for binding can be placed. The term "container" encompasses reaction tubes (e.g., test tubes, microtubes, vials, etc.).

The term "biological sample" refers to the contents of a container.

"Spectral emission," "thermal change," and "physical change" encompass the release of energy in the form of light or heat, the absorption of energy in the form or light or heat, changes in turbidity and changes in the polar properties of light. Specifically, the terms refer to fluorescent emission, fluorescent energy transfer, absorption of ultraviolet or visible light, changes in the polarization properties of light, changes in the polarization properties of fluorescent emission, changes in the rate of change of fluorescence over time (i.e., fluorescence lifetime), changes in fluorescence anisotropy, changes in fluorescence resonance energy transfer, changes in turbidity, and changes in enzyme activity. Preferably, the terms refer to fluorescence, and more preferably to fluorescence emission. Fluorescence emission can be intrinsic to a protein or can be due to a fluorescence reporter molecule. The use of fluorescence techniques to monitor protein unfolding is well known to those of ordinary skill in the art. For example, see Eftink, M. R., Biophysical J. 66:482-501 (1994).

"Biochemical conditions" encompass any component of a physical, chemical, or biochemical reaction. Specifically, the term refers to conditions of temperature, pressure, protein concentration, pH, ionic strength, salt concentration, time, electric current, potential difference, concentrations of cofactor, coenzyme, oxidizing agents, reducing agents, detergents, metal ion, ligands, or glycerol.

It is therefore intended that the foregoing detailed description be regarded as illustrative rather than limiting, and that it be understood that it is the following claims, including all equivalents, that are intended to define the spirit and scope of this invention.

Compounds That Have a Fluorescent Readout

The compounds of the present invention undergo enhanced fluorescence in nonpolar environments as compared to polar environments. Examples of nonpolar environments include nonpolar solvents and hydrophobic proteins or membranes.

Compounds

Compounds in accordance with the present invention are of the formula (I):

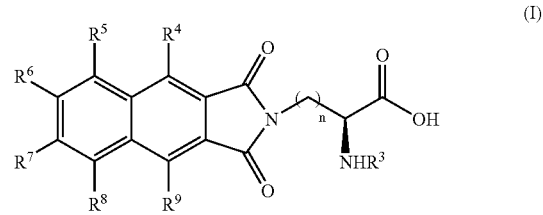

where $R^4$, $R^5$, $R^6$, $R^7$, $R^8$, and $R^9$ are each independently hydrogen, fluorine, or alkyl, with the proviso that one of $R^6$ or $R^7$ is $-NR^1R^2$, $-OR^1$, or $-SR^1$;

$R^1$ and $R^2$ are each independently hydrogen or alkyl; or $R^1$ and $R^2$ together with the nitrogen to which they are attached, may form a substituted or unsubstituted 5- or 6-membered ring; wherein said nitrogen is not conjugated with said 5- or 6-membered ring;

$R^3$ is hydrogen or a N-protecting group;

n is 1, 2, 3 or 4.

Preferably one of $R^6$ or $R^7$ is $-NR^1R^2$. More preferably, $R^7$ is $-NR^1R^2$. Preferably, $R^1$ or $R^2$ is alkyl. More preferably, $R^1$ and $R^2$ are both alkyl. Even more preferably, $R^1$ and $R^2$ are both methyl, ethyl or propyl. Preferably, $R^1$ and $R^2$ together with the nitrogen to which they are attached are pyrrolidinyl, piperdinyl, or morpholinyl. Preferably $R^3$ is a N-protecting group. More preferably $R^3$ is Boc, Cbz, or Fmoc. Even more preferably $R^3$ is Fmoc.

In a preferred embodiment, the compound of the present invention can have the formula (II):

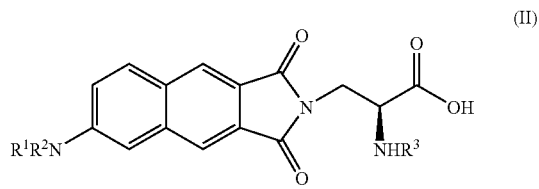

(II)

where $R^1$, $R^2$, and $R^3$ are described above for formula (I).

In another embodiment, the compound of the present invention can have the formula (IV):

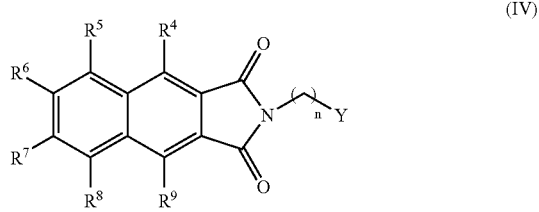

(IV)

where n, $R^4$, $R^5$, $R^6$, $R^7$, $R^8$, and $R^9$ are described above for formula (I);

Y is $NH_2$ or $C(O)X$; and

X is halogen, hydroxy or alkoxy.

In another embodiment, the compound of the present invention can have the formula (V):

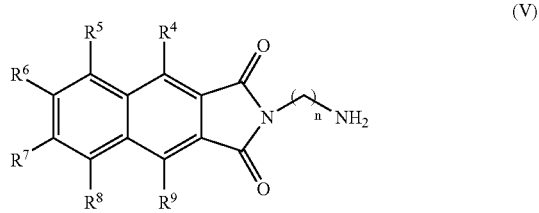

(V)

where n, $R^4$, $R^5$, $R^6$, $R^7$, $R^8$, and $R^9$ are described above for formula (I).

In another embodiment, the compound of the present invention can have the formula (VI):

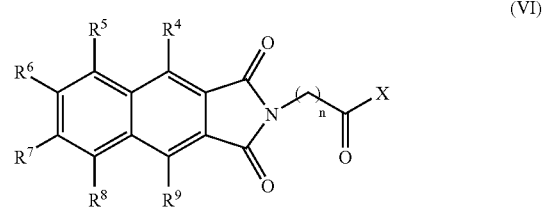

(VI)

where n, $R^4$, $R^5$, $R^6$, $R^7$, $R^8$, and $R^9$ are described above for formula (I) and X is described in formula (IV).

In another embodiment, the compound of the present invention can have the formula (VII):

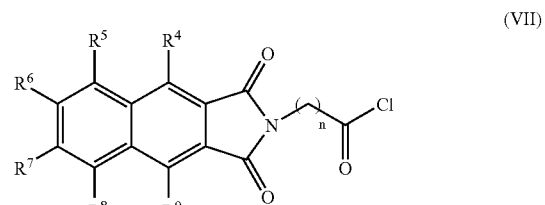

(VII)

where n, $R^4$, $R^5$, $R^6$, $R^7$, $R^8$, and $R^9$ are described above for formula (I).

In another embodiment, the compound can have the formula (VIII):

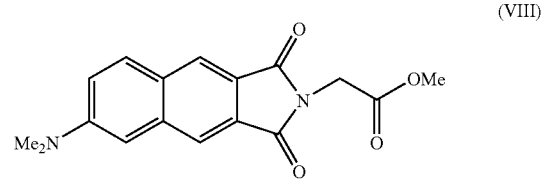

(VIII)

In another embodiment, the compound can be a peptide containing the formula (I):

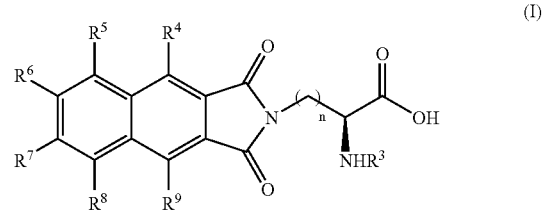

(I)

where n, $R^1$, $R^2$, $R^3$, $R^4$, $R^5$, $R^6$, $R^7$, $R^8$, and $R^9$ are described above for formula (I).

In another preferred embodiment, the compound can be a peptide containing the formula (II):

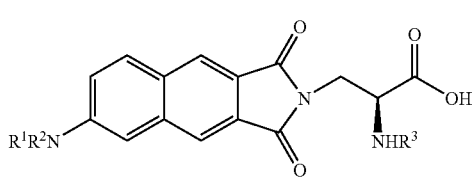

(II)

where $R^1$, $R^2$, and $R^3$ are each described above for formula (I).

In another preferred embodiment, the compound can be a peptide containing the formula (III):

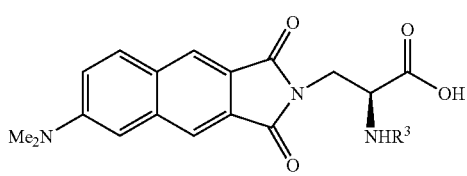

(III)

where $R^3$ is described above for formula (I). When $R^3$ is hydrogen, compound (III) is referred to herein as Dap (6DMN). When $R^3$ is Fmoc, compound (III) is herein referred to as Fmoc-Dap(6DMN).

Uses of Compounds

Compounds of the present invention are useful as fluorescence probe molecules in applications wherein fluorescence probes are known to be useful. In using a compound of the present invention as a fluorescence probe molecule, the compound is added to a sample to be probed. The sample comprising the compound is then exposed to a light source. The light source produces light that is limited to a range of wavelengths. The range of wavelengths is between about 360 and about 410 nanometers (nm), preferably between about 370 and about 390 nm, most preferably between about 375 and about 380 nm. Upon exposure to a light source, the compound of the present invention is fluorescent and emits fluorescent energy. The emitted fluorescent energy is detected using methods well known in the art. The intensity and wavelength of the emitted fluorescent energy provides information about the sample. The emitted fluorescent energy preferably has a range of wavelengths between about 480 and about 640 nm, preferably between about 560 and about 590 nm.

The fluorescence of a molecule is defined by the quantum yield. The quantum yield is the ratio of the photons absorbed by the compound to the photons emitted through fluorescence by the compound. Compounds of the present invention have quantum yields that are preferably low in aqueous solutions and high in non-polar environments. Quantum yields range from about 0.001 and about 0.1, preferably between about 0.001 and about 0.005 for aqueous solutions, preferably between about 0.2 and about 0.7 for non-polar environment.

Fluorescence can also be evaluated by determining the dipole moment change between the ground and excited state. The change in the dipole moment can be estimated from a plot of the Stokes shift vs. the orientation polarizability, known as a Lippert-Mataga plot. (Lippert, V. E. *Z. Elektrochem.* 1957, 61, 962-975; Mataga, N.; Kaifu, Y.; Koizumi, M. *Bull. Chem. Soc. Jpn.* 1956, 29, 465-470.) The relationship between the Stokes shift ($\Delta \bar{v}$) and the orientation polarizability ($\Delta f$) and is expressed by the following equation:

$$\bar{v}_A - \bar{v}_F = \Delta \bar{v} \quad (5)$$
$$= \frac{2}{hca_0^3}\left(\frac{\varepsilon - 1}{2\varepsilon + 1} - \frac{n^2 - 1}{2n^2 + 1}\right)(\mu_e - \mu_g)^2$$
$$= \frac{2\Delta f}{hca_0^3}\Delta\mu^2$$

where c is the velocity of light, h is Plank's constant, $\epsilon$ is the solvent dielectric constant, n is the solvent refraction index, $\mu_e - \mu_g$ is the difference between the dipole moments of the excited and the ground states respectively ($\Delta\mu$), and $\alpha_0$ is the radius of the Onsager cavity around the compound. The magnitude of $\Delta\mu$ correlates to the sensitivity of the fluorescent probe, where larger changes in the dipole moment correlate to greater sensitivity.

Fluorescence is sensitive to the pH of the surrounding environment. Compounds of the present invention are useful as fluorescence probes in the pH range from about 4 to about 8.

Compounds of the present invention are useful in monitoring biological interactions. Biological interactions play important roles in the sequence and mechanisms of action of various cellular processes and signal pathways. The time course, nature, and sequence of the different cellular processes can be elucidated by in situ observation using the compounds of the present invention. Specific inhibitors and/or activators of the cellular processes and signal pathways being studied may optionally be used in addition to compounds of the present invention.

Biological interactions, as defined herein, comprise the interaction of a compound or molecule with a target molecule. Examples of target molecules include peptides, proteins, enzymes, nucleic acids, ions, and other receptors; preferably metal ion chelators, proteases, polymerases, hydrolases, phosphatases, and kinases; more preferably protein domains, and protein domains of phosphatases and kinases.

Proteins and protein-protein interactions play a central role in the various essential biochemical processes. For example, these interactions are evident in the interaction of hormones with their respective receptors, in the intracellular and extracellular signaling events mediated by proteins, in enzyme substrate interactions, in intracellular protein trafficking, in the formation of complex structures like ribosomes, viral coat proteins, and filaments, and in antigen-antibody interactions. These interactions are usually facilitated by the interaction of small regions within the proteins that can fold independently of the rest of the protein. These independent units are called protein domains. Abnormal or disease states can be the direct result of aberrant protein-protein interactions. Protein-protein interactions are also central to the mechanism of a virus recognizing its receptor on the cell surface as a prelude to infection. Identification of domains that interact with each other not only leads to a broader understanding of protein-protein interactions, but also aids in the design of inhibitors of these interactions.

Phosphorylation-dependent peptide-protein interactions include phosphoserine peptides with 14-3-3, which is a protein involved in cell cycle control (Muslin, A. J., Tanner, J. W., Allen, P. M., Shaw, A. S. *Cell* 1996, 84, 889-897.), and phosphotyrosine peptides with SH2 domains. SH2 domains are binding modules that are involved in tyrosine kinase signaling networks and recognize phosphotyrosine-containing peptide sequences. The phosphotyrosine binding is complemented by simultaneous peptide-protein interactions on the protein surface. Examples of SH2 domains include Abl SH2, Crk SH2, and C-terminal P13K SH2 which can be expressed in bacteria as GST fusion proteins, which are referred to as GST-Abl SH2, GST-Crk SH2, and GST-PI3K SH2.

Recognition sequences for SH2 domains comprise a phosphotyrosine residue and other amino acids. The recognition sequence is different for different SH2 domains. Amino acid recognition sequences for binding members of the SH2 domain family are disclosed in Songyang, Z. et al.; *Cell* 1993, 72, 767-778. For the Crk SH2 domain, the recognition sequence is pTyr-Asp-His-Pro. For the Abl SH2 domain, the recognition sequence is pTyr-Glu-Asn-Val.

Compounds of the formula (I) are useful for studying the peptide-protein interactions on the protein surface of the SH2 domain. Compounds of formula (I) can be incorporated into peptides containing the desired SH2 recognition sequence. Table 1 shows peptides incorporating the Crk SH2 or Abl SH2 recognition sequences and Dap(6DMN) into the (+2) position relative to the phosphotyrosine residue.

TABLE 1

Peptide Sequences and Corresponding SH2 Domain Target

| Peptide | Target SH2 | Peptide sequence |
|---------|------------|------------------|
| Crk-bp | Crk | Ac-Glu-Dap(6DMN)-Gln-pTyr-Asp-His-Pro-Asn-Ile-(CONH$_2$) (SEQ ID NO: 1) |
| Crk-bp2 | Crk | Ac-Gly-Dap(6DMN)-Gly-pTyr-Asp-His-Pro-Asn-Ile-(CONH$_2$) (SEQ ID NO: 2) |
| Abl-bp | Abl | Ac-Glu-Dap(6DMN)-Gly-pTyr-Glu-Asn-Val-Gln-Ser-(CONH$_2$) (SEQ ID NO: 3) |
| Abl-bp2 | Abl | Ac-Glu-Dap(6DMN)-pTyr-Glu-Asn-Val-Gln-Ser-(CONH$_2$) (SEQ ID NO: 4) |

The peptides of Table 1 were incubated with targeted and nontargeted SH2 domains. The binding of peptides Crk-bp, Crk-bp2, Abl-bp, and Abl-bp2 to SH2 target domains can be studied by fluorescence titration as shown in FIGS. 1-4.

Figure 4:
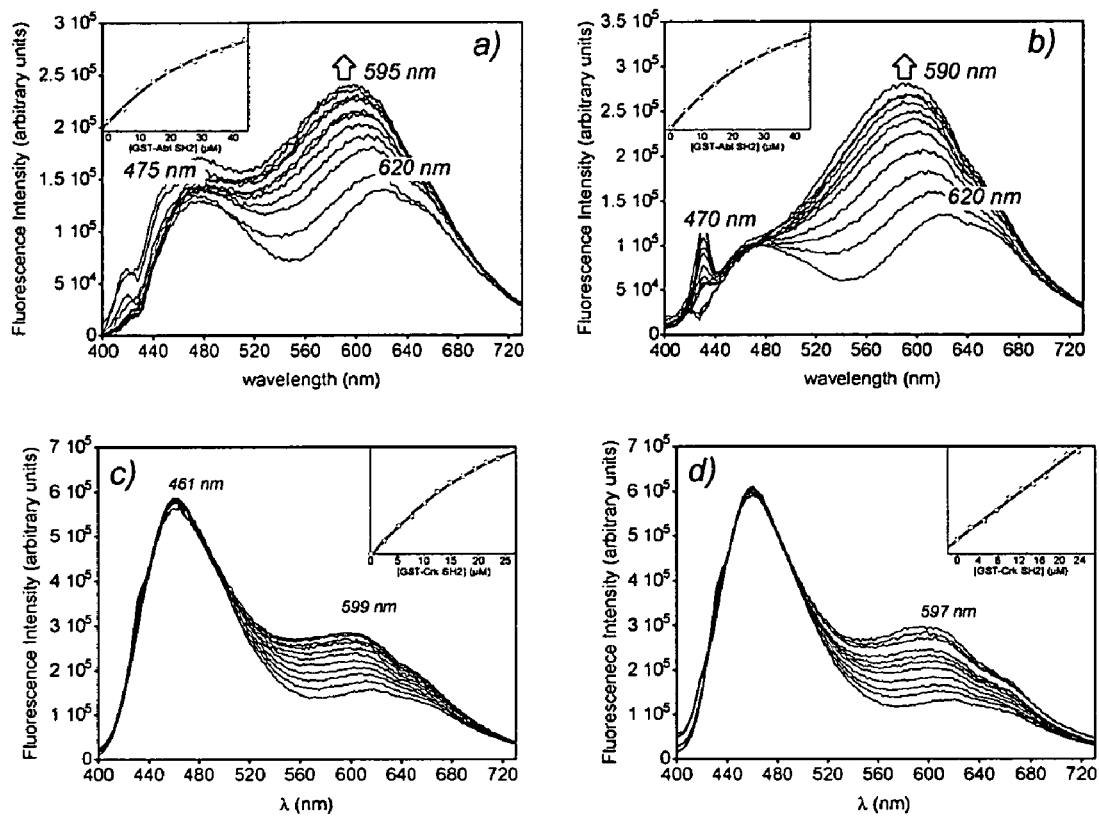
FIG. 4 are graphs depicting fluorescence titrations of peptides with non-target SH2 domains. a) Crk-bp with GST-Abl SH2, b) Crk-bp2 with GST-Abl SH2, c) Abl-bp with GST-Crk SH2, d) Abl-bp2 with GST-Crk SH2.

Fluorescence titrations of Crk-bp and Crk-bp2 with targeted GST-Crk SH2 are shown in FIG. 1 (*a*) and (*b*), respectively. Fluorescence titrations of Crk-bp and Crk-bp2 with non-targeted GST-Abl SH2 are shown in FIG. 4 (*a*) and (*b*), respectively. FIG. 1 (*c*) shows relative fluorescence emission intensities for Crk-bp and Crk-bp2 peptides, Crk-bp and Crk-bp2 bound to GST-Crk SH2 domain, and Crk-bp2 bound to non-target domains GST-Abl SH2 and GST-PKI3 SH2. The relative fluorescence emission intensities for non-target SH2 domains is notably less than for the targeted GST-Crk SH2 domain.

Figure 2:
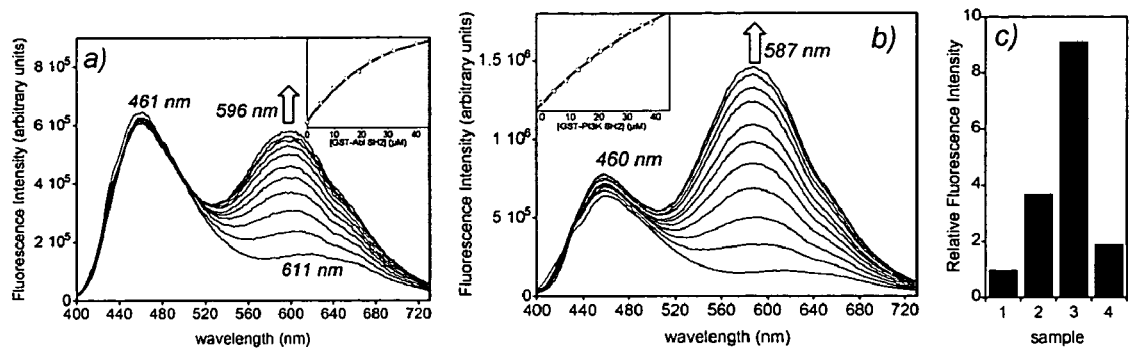
FIG. 2 are fluorescence titrations of peptide Abl-bp with various GST SH2 domains. (a) Abl-bp (20 μM in PBS buffer, pH 7.5) with GST-Abl SH2. (b) Abl-bp (20 μM in PBS buffer, pH 7.5) with GST-PI3K SH2. Inserts show plots of the fluorescence emission intensity at 599 nm, with the best fitting binding curves. Spectra were corrected for the dilution upon addition of the protein solution. (c) Relative fluorescence emission intensities at 590 nm for: 1) Peptide Abl-bp. 2) Peptide Abl-bp saturated with GST-Abl SH2 and 3) Peptide Abl-bp saturated with GST-PI3K SH2. 4) Peptide Abl-bp saturated with GST-Crk SH2. (GST-PI3K SH2 and GST-Crk SH2 are not-target SH2 domains for the peptide Abl-bp.)

Fluorescence titrations of Abl-bp with targeted GST-Abl SH2 is shown in FIG. 2 (*a*). Fluorescence titrations of Abl-bp with non-targeted GST-PI3K SH2 and GST-Abl SH2 are shown in FIG. 2 (*b*) and 4 (*c*), respectively. The relative fluorescence emission intensities for the Abl-bp peptide and aforementioned SH2 domain titrations are shown in FIG. 2 (*c*).

Figure 3:
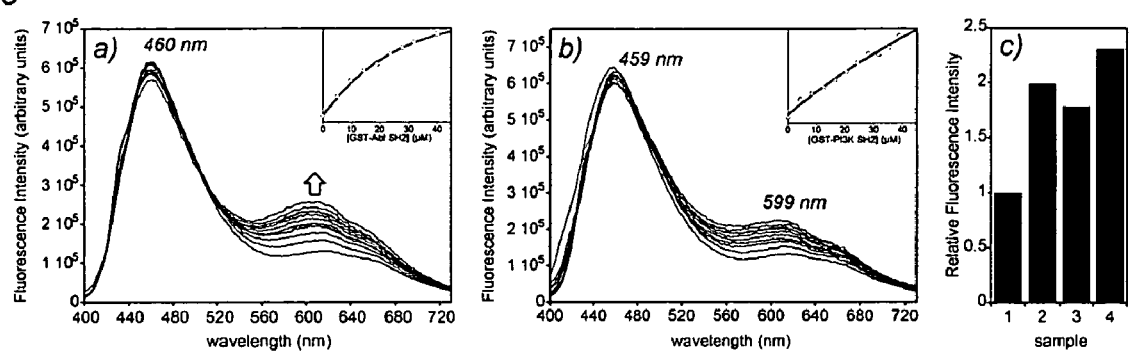
FIG. 3 are fluorescence titrations of peptide Abl-bp2 with various GST SH2 domains. (a) Abl-bp2 (20 μM in PBS buffer, pH 7.5) with GST-Abl SH2. (b) Abl-bp2 (20 μM in PBS buffer, pH 7.5) with GST-PI3K SH2. Inserts show plots of the fluorescence emission intensity at 599 nm, with the best fitting binding curves. Spectra were corrected for the dilution upon addition of the protein solution. (c) Relative fluorescence emission intensities at 599 nm for: 1) Peptide Abl-bp2. 2) Peptide Abl-bp2 saturated with GST-Abl SH2 and 3) Peptide Abl-bp2 saturated with GST-PI3K SH2. 4) Peptide Abl-bp2 saturated with GST-Crk SH2. (GST-PI3K SH2 and GST-Crk SH2 are not-target SH2 domains for the peptide Abl-bp.2)

Fluorescence titrations of Abl-bp2 with targeted GST-Abl SH2 is shown in FIG. 3 (*a*). Fluorescence titrations Abl-bp2 with non-targeted GST-PI3K SH2 and GST-Crk SH2 are shown in FIGS. 3 (*b*) and 4 (*d*), respectively. The relative fluorescence emission intensities for the Abl-bp2 peptide and aforementioned SH2 domain titrations are shown in FIG. 3 (*c*).

TABLE 2

Kinetic and Fluorescence Properties of Peptides containing Dap(6DMN)

| Peptide | Target SH2 | Peptide Sequence | $K_d$(μM) | Fluorescence increase |
|---------|------------|------------------|-----------|----------------------|
| Crk-bp | Crk | Ac-Glu-Dap(6DMN)-Gln-pTyr-Asp-His-Pro-Asn-Ile-(CONH$_2$) (SEQ ID NO: 1) | 4.8 ± 2[a] | 500%[b] |
| Crk-bp2 | Crk | Ac-Gly-Dap(6DMN)-Gln-pTyr-Asp-His-Pro-Asn-Ile-(CONH$_2$) (SEQ ID NO: 5) | 2.4 ± 2[a] | 1100%[b] |
| Abl-bp | Abl | Ac-Gly-Dap(6DMN)-Gln-pTyr-Glu-Asn-Val-Gln-Ser-(CONH$_2$) (SEQ ID NO: 6) | 13 ± 2[a] | 400%[c] |
| Abl-bp2 | Abl | Ac-Dap(6DMN)-Gln-pTyr-Glu-Asn-Val-Gln-Ser-(CONH$_2$) (SEQ OD NO: 7) | 12 ± 2[a] | — |

[a]Assay conditions: 20 μM in PBS buffer, pH 7.5.
[b]Excitation wavelength: 375 nm, Emission wavelength, 565 nm.
[c]Excitation wavelength: 375 nm, Emission wavelength, 599 nm.

Compounds of the present invention are also useful in a method of monitoring biological interactions, comprising providing a compound of the present invention, contacting a target molecule with the compound to form a biological sample, and monitoring the fluorescence of the biological sample. Preferably, the compound is a peptide. More preferably, the compound is a peptide containing at least one of formula (I), (II), and (III).

In the methods of the present invention, the monitoring step comprise contacting the compound with the one or more target molecules or different biochemical conditions, wherein the measuring step comprises exciting the compound of the present invention with light, and measuring the fluorescence.

In all methods of using a compound of the present invention, the concentration used will depend on the detection equipment. Typically, the concentration of the compound is from greater than about 0.1 nM.

Preparation of Compounds

The compounds of formula (I) can be prepared according to the reaction as shown in Scheme 1, wherein, n, $R^3$, $R^4$, $R^5$, $R^6$, $R^7$, $R^8$ and $R^9$ are as defined above. Anhydride (1) is stirred with an appropriate diamine (2) in a suitable solvent to form compound 3. The allyl protecting group of compound 3 can be removed under standard conditions known to those skilled in the art, examples of which are disclosed in Greene and Wuts, *Protective Groups in Organic Synthesis* 2nd ed.; John Wiley & Sons, New York, 1991) to afford a compound of Formula I (4). The diamine compound 2 can be prepared from the corresponding diamino acid using standard conditions for protecting a carboxylic acid with an allyl protecting group known to those skilled in the art, examples of which are provided in Greene and Wuts.

Scheme 1

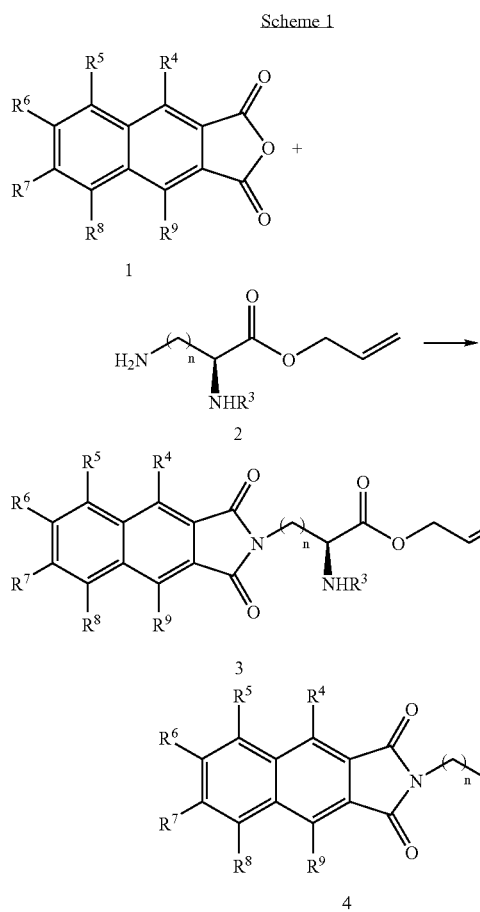

Anhydride 1 can be prepared by stirring diester 5 with an appropriate base in a suitable solvent. Compound 5 can be assembled by methods known to one skilled in the art such ring annulation methods or Diels-Alder reaction.

Scheme 2

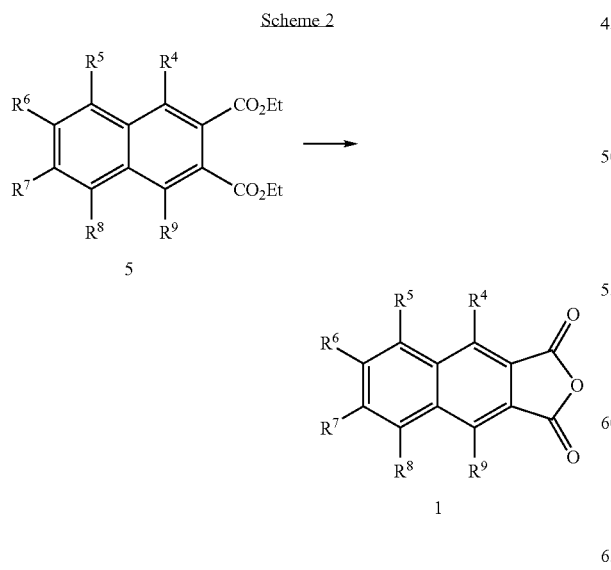

The compounds of formula (IV) can be prepared by stirring anhydride (1) with an appropriate amine in a suitable solvent to form compounds of formula (IV), wherein, n, $R^4$, $R^5$, $R^6$, $R^7$, $R^8$, $R^9$ and Y are as defined above. In the case where Y is $NH_2$, the amine is diamino compound (6) as shown in Scheme 3 which is stirred with anhydride (1) to for compound (7). Diamines are commercially available from vendors such as Aldrich, for example. Alternatively, compound 7 may be prepared by stirring anhydride (1) with a diamine where one of the nitrogens is protected with a suitable N-protecting group. After formation of the imide bond, the N-protecting group can be removed to afford compound (7). Methods for introduction and removal of N-protecting groups are known to those skilled in the art, examples of which are disclosed in Greene and Wuts, *Protective Groups in Organic Synthesis*, 2nd ed.; John Wiley & Sons, New York, 1991.

Scheme 3

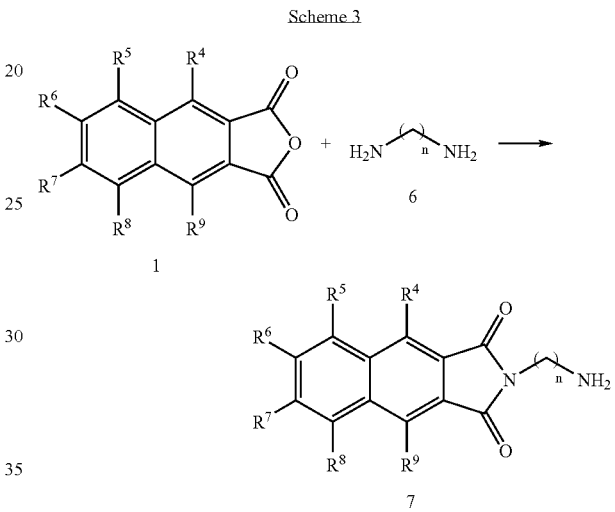

The compounds of formula (IV) wherein, n, $R^4$, $R^5$, $R^6$, $R^7$, $R^8$, $R^9$ are as defined above as Y is C(O)X, can be prepared as shown in scheme 4. Amino acid 8 can be carboxylprotected with a suitable protecting group, then stirred with anhydride (1) in a suitable solvent. Removal of the carboxylprotecting group under standard conditions afford compound (9). Methods for introduction and removal of N-protecting groups are known to those skilled in the art, examples of which are disclosed in Greene and Wuts, *Protective Groups in Organic Synthesis*, 2nd ed.; John Wiley & Sons, New York, 1991. Compound (10) where X is halogen or alkoxy can be prepared under standard conditions acyl halide (*Org. Syn. Coll. Vol.* 1 1941, 12, 147; *Org. Syn. Coll. Vol.* 3 1955, 169, 490, 547, 555, 712; *Org. Syn. Coll. Vol* 4 1963, 154, 263, 339, 715, 739) or esterification (*Tetrahedron.* 1980, 36, 2409) conditions.

Scheme 4

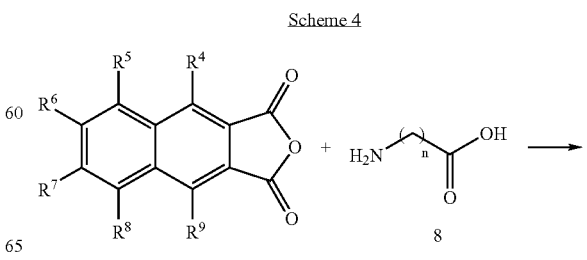

-continued

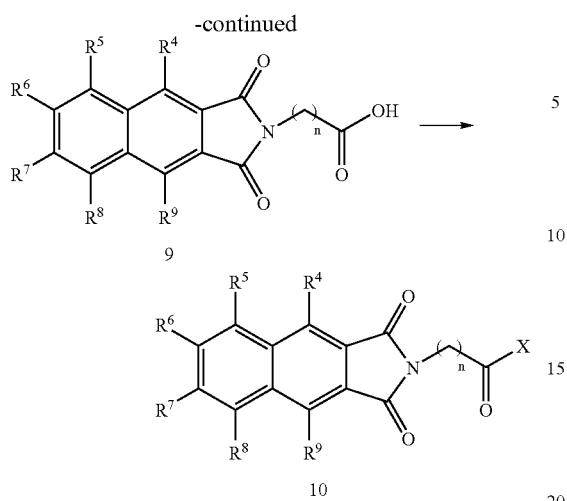

Peptides containing the formula (I) can be prepared using standard peptide coupling techniques known to those skilled in the art. Examples are provided in Bodansky, M. *Peptide Chemistry a Practical Textbook*, 2nd ed.; Springer-Verlag, Berlin, 1993. Dap(6DMN), can incorporated into peptides using Fmoc-Dap(6DMN) and standard Fmoc solid-phase peptide synthesis.

The sensor of the present invention can be used in a method for detecting biological interactions. The method of the present invention comprises providing a peptide incorporating an amino acid of the formula (I), contacting a target molecule with the peptide to form a biological sample, and monitoring the fluorescence of the biological sample.

It is therefore intended that the foregoing detailed description be regarded as illustrative rather than limiting, and that it be understood that it is the following claims, including all equivalents, that are intended to define the spirit and scope of this invention.

EXAMPLES

General Procedures:

All peptide synthesis reagents and amino acid derivatives were purchased from Applied Biosystems or Novabiochem. All other chemicals were purchased from Aldrich. Dichloromethane was distilled from calcium hydride under nitrogen, and tetrahydrofuran was distilled from sodium under argon. Analytical thin-layer chromatography (TLC) was carried out on F254 250-μm silica gel plates, and visualized by UV.

$^1$H and $^{13}$C NMR spectra were acquired on a 400 MHz Bruker spectrometer. NMR samples were prepared in deuterated chloroform (CDCl$_3$) unless otherwise stated. Chemical shifts are reported in ppm relative to the internal standard (tetramethyl silane for $^1$H), and J values are reported in Hz. Electrospray Ionization Mass Spectrometry (ESIMS) was performed on a PerSeptive Biosystems Mariner™ Biospectrometry Workstation (Turbo Ion Source). Fluorescence spectroscopy measurements were made using a Fluoromax-P spectrofluorimeter controlled by the DataMax 2.20 software, and coupled to a NesLab RTE-111 water bath for temperature control. All measurements were made at 20° C.

6-(Dimethylamino)-2,3-naphthalenedicarboxylic anhydride:

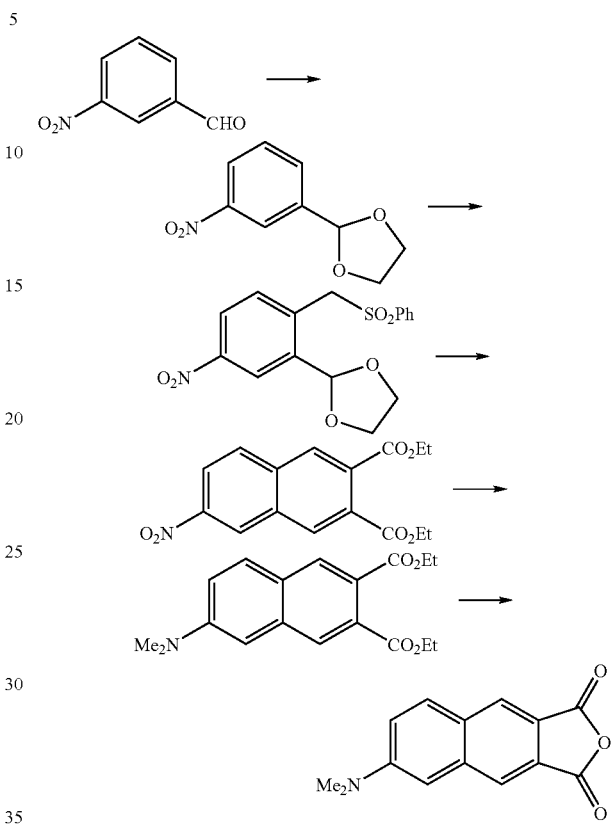

Protection of the aldehyde was performed following reported procedures. (Borchardt, R. T.; Huber, J. A.; Houston, M. J. *Med. Chem.* 1982, 25, 258.; Brasili, L.; Sorbi, C.; Franchini, S.; Manicardi, M.; Angeli, P.; Marucci, G.; Leonarke, A.; Poggesi, E. *J. Med. Chem.* 2003, 46, 1504) 3-Nitrobenzaldehyde (4.0 g, 26.4 mmol) was dissolved in toluene (200 mL). Following this, ethanediol (3.0 mL, 53 mmol, 2.0 eq) was added to the solution and the resulting mixture was refluxed overnight with a Dean-Stark trap. The reflux mixture was then extracted with saturated NaHCO$_3$ (2×75 mL). The organic layer was dried with Na$_2$SO$_4$ and concentrated under reduced pressure. The residue was then purified by flash column chromatography (30% EtOAc/hexanes) to afford 3-nitrophenyl-1,3-dioxolane as a clear yellow oil that solidified upon standing. (5.09 g, 98%, R$_f$=0.7 40% EtOAc/hexanes). $^1$H-NMR (400 MHz, CDCl$_3$, δ): 4.0-4.2 (m, 4H), 5.87 (s, 1H), 7.55 (t, 1H, J=7.93 Hz), 7.79 (d, 1H, J=7.7 Hz), 8.21 (dd, 1H, J$_1$=1.2 Hz, J$_2$=8.2 Hz), 8.34 (s, 1H). $^{13}$C-NMR (100 MHz, CDCl$_3$, δ): 148.4, 140.5, 132.8, 129.6, 124.1, 121.8, 102.3, 65.6.

3-Nitrophenyl-1,3-dioxolane (1.0 g, 5.1 mmol) and chloromethyl-phenyl sulfone (975 mg, 5.1 mmol) were dissolved in dry dimethyl sulfoxide. Then, KOH powder (2.00 g) was added to the solution, which immediately turned dark purple. The resulting mixture was stirred overnight at room temperature, then poured over 75 mL 2% aqueous HCl and extracted with EtOAc (3×50 mL). The combined organic layers were dried with Na$_2$SO$_4$ and concentrated under reduced pressure to give a dark brown oil that was purified by flash column chromatography (30% EtOAc/hexanes). Two regioisomeric products were isolated. The combined yield of the reaction is 1.23 g (35% desired product, $R_f$=0.4 40% EtOAc/hexanes). Compounds ortho- and para- could be identified by the $^1$H-NMR signals of the protons ortho- to the nitro group. In the case of the desired compound, 2-(2-phenylsulfonylmethyl-5-nitrophenyl)-1,3-dioxolane, both signals are present in the NMR spectra. $^1$H-NMR (400 MHz, CDCl$_3$, δ): 4.01 (s, 4H), 4.73 (s, 2H), 5.93 (s, 1H), 7.32 (d, 1H, J=8.3 Hz), 7.53 (t, 2H, J=7.6 Hz), 7.67 (t, 1H, J=7.7 Hz), 7.72 (d, 2H, J=7.6 Hz), 8.10 (d, 1H, J=6.6 Hz), 8.45 (s, 1H). $^{13}$C-NMR (100 MHz, CDCl$_3$, δ): 148.1, 140.7, 138.2, 134.5, 133.7, 129.5, 128.6, 123.6, 121.7, 100.2, 65.5, 59.0. HRMS-ESI (m/z): [M+H$^+$] calcd for C$_{16}$H$_{15}$NO$_6$S 350.0693, found, 350.0677.

2-(2-Phenylsulfonylmethyl-5-nitrophenyl)-1,3-dioxolane (400 mg, 1.14 mmol) was dissolved in AcOH (8 mL) and water (2 mL). The solution was refluxed for 5 h and then concentrated under reduced pressure. The resulting solid was confirmed as the desired product by NMR and used in the next step without further purification. In a 25 mL round bottom flask, 5-nitro-2-phenylsufonylmethylbenzaldehyde (300 mg, 1.00 mmol), diethylmaleate (195 μL, 207 mg, 1.20 mmol) and 18-crown-6 (13 mg, 0.05 mmol) were dissolved in acetonitrile (10 mL). K$_2$CO$_3$ (700 mg) was added and the resulting mixture was stirred for 30 min. The reaction was refluxed for 3 h, then filtered over celite and concentrated under reduced pressure. The resulting dark oily residue was purified by flash chromatography (30% EtOAc/hexanes) to give diethyl 6-nitro-2,3-naphthalenedicarboxylate (231 mg, 64%, $R_f$=0.35 20% EtOAc/hexanes). $^1$H-NMR (400 MHz, CDCl$_3$, δ): 1.42 (t, 3H, J=7.1 Hz), 1.43 (t, 3H, J=7.1 Hz), 4.45 (c, 4H, J=7.1 Hz), 8.07 (d, 1H, J=9.0 Hz), 8.31 (s, 1H), 8.37 (dd, 1H, J$_1$=9.0 Hz, J$_2$=2.1 Hz), 8.47 (s, 1H), 8.87 (d, 1H, J=1.8 Hz). $^{13}$C-NMR (100 MHz, CDCl$_3$, δ): 167.1, 166.7, 147.2, 135.9, 132.8, 132.3, 131.9, 130.9, 130.5, 129.9, 129.7, 125.13, 121.9, 62.36, 14.33. HRMS-ESI (m/z): [M+H$^+$] calcd for C$_{16}$H$_{15}$NO$_6$ 318.0972, found, 318.0986.

Diethyl 6-nitro-2,3-naphthalenedicarboxylate (350 mg, 1.11 mmol) was dissolved in MeOH (50 mL). Formalin (7 mL) was added and Pd/C 10% (100 mg) was added to the solution. The resulting mixture was stirred under hydrogen for 2.5 h until TLC showed that the starting material has been consumed. The reaction mixture was then filtered through celite and partly concentrated to approximately 20 mL. Following this, the mixture was poured over 2% aqueous NaHCO$_3$ (150 mL) and extracted (3×50 mL EtOAc). The combined organic layers were dried with Na$_2$SO$_4$ and concentrated under reduced pressure to give diethyl 6-(dimethylamino)-2,3-naphthalenedicarboxylate (295 mg, 84%, $R_f$=0.5 30% EtOAc/hexanes). $^1$H-NMR (400 MHz, CDCl$_3$, δ): 1.38 (t, 3H, J=7.1 Hz), 1.39 (t, 3H, J=7.1 Hz), 3.03 (s, 6H), 4.37 (c, 2H, J=7.1 Hz), 4.40 (c, 2H, J=7.1 Hz), 6.84 (s, 1H), 7.15 (dd, 1H, J$_1$=9.1 Hz, J$_2$=2.5 Hz), 7.7 (d, 1H, J=9.1 Hz), 7.88 (s, 1H), 8.17 (s, 1H). $^{13}$C-NMR (100 MHz, CDCl$_3$, δ): 169.1, 167.6, 150.16, 135.7, 130.7, 130.4, 129.8, 127.4, 125.7, 123.2, 117.6, 105.8, 61.5, 61.3, 40.4, 14.4, 14.3. HRMS-ESI (m/z): [M+H$^+$] calcd for C$_{18}$H$_{21}$NO$_4$ 316.1549, found, 316.1556.

Diethyl 6-(dimethylamino)-2,3-naphthalenedicarboxylate (373 mg, 1.2 mmol), was refluxed in 1:5 MeOH:40% KOH (25 mL) for 3 h. The reaction mixture was then poured over water (150 mL), acidified with 6 M HCl to pH 2 and extracted with EtOAc (5×30 mL). The combined organic layers were dried with Na$_2$SO$_4$ and concentrated under reduced pressure. The resulting solid residue, corresponding to the diacid intermediate, was used in the next step without purification (228 mg, 85%). The diacid was placed in a sublimation apparatus and heated at 175° C. under vacuum for 4 h. 6-(Dimethylamino)-2,3-naphthalenedicarboxylic anhydride was recovered after sublimation as a bright yellow solid (213 mg, 77% overall yield, $R_f$=0.6 40% EtOAc/hexanes). $^1$H-NMR (400 MHz, CDCl$_3$, δ): 3.19 (s, 6H), 7.02 (d, 1H, J=2.4 Hz), 7.34 (dd, 1H, J$_1$=9.2 Hz, J$_2$=2.6 Hz), 7.92 (d, 1H, J=9.2 Hz), 8.20 (s, 1H), 8.30 (s, 1H). HRMS-ESI (m/z): [M+H$^+$] calcd for C$_{14}$H$_{11}$NO$_3$ 242.0812, found, 242.0805. For diacid intermediate: HRMS-ESI (m/z): [M+H$^+$] calcd for C$_{14}$H$_{13}$NO$_4$ 258.0772, found, 252.0764.

Fmoc-Dap(6DMN):

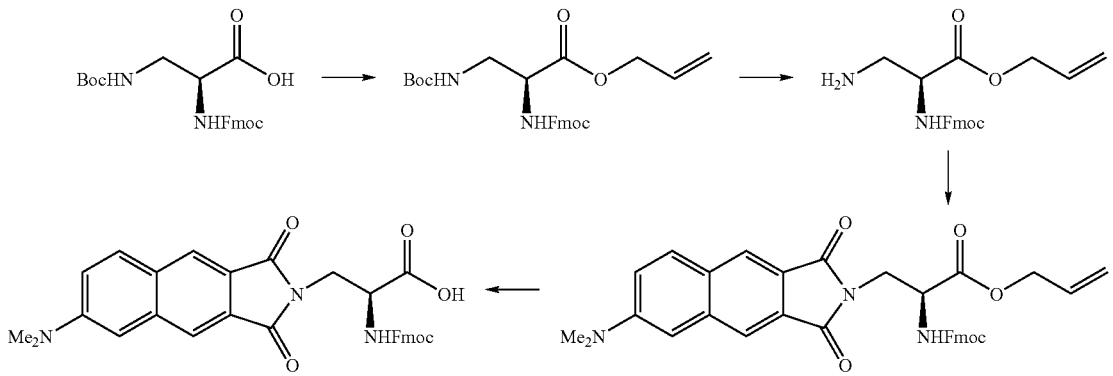

Fmoc-Dap(Boc)-OH (450 mg, 1.05 mmol) was dissolved in MeOH (15 mL). Cs$_2$CO$_3$ (172 mg, 0.53 mmol) was added and the resulting solution was stirred at room temperature for 10 minutes. The reaction mixture was concentrated under reduced pressure and redissolved in DMF (30 mL). Allyl bromide (280 μL, 3.3 mmol) was added and the mixture was stirred for 1 h at room temperature. The reaction was poured over 2% aqueous NaHCO$_3$ (150 mL) and extracted with EtOAc (4×50 mL). The combined organic layers were dried with Na$_2$SO$_4$ and concentrated under reduced pressure. The resulting brown oily residue was purified by flash column chromatography (1% MeOH/CH$_2$Cl$_2$, $R_f$=0.6 5% MeOH/CH$_2$Cl$_2$) to give allyl N-α-Fmoc-N-β-Boc-L-diaminopropionate as a white powder (516 mg, 78%). $R_f$=0.7 (1% MeOH/CH$_2$Cl$_2$). $^1$H NMR (400 MHz, CDCl$_3$, δ): 1.34 (s, 9H), 3.48 (br s, 2H), 4.12 (br s, 1H), 4.2-4.4 (m, 2H), 4.55 (br s, 2H), 4.9 (br s, 1H), 5.14 (d, 1H, J=10.3 Hz), 5.22 (d, 1H, J=17.1 Hz), 5.8 (brs, 1H), 5.9 (d, 1H, 5.8 Hz), 7.18 (t, 2H, J=7.3 Hz), 7.27

(t, 2H, J=7.4 Hz), 7.5 (br s, 2H), 7.65 (d, 2H, J=7.4 Hz). $^{13}$C NMR (400 MHz, CDCl$_3$, δ): 170.4, 156.6, 156.2, 143.8, 141.4, 131.6, 127.8, 127.2, 125.3, 120.9, 119.1, 80.1, 67.3, 66.5, 55.3, 47.2, 42.2, 28.4. HRMS-ESI (m/z): [M+H$^+$] calcd for C$_{26}$H$_{30}$N$_2$O$_6$ 467.2177, found, 467.2177.

Allyl N-α-Fmoc-N-β-Boc-L-diaminopropionate (175 mg, 0.38 mmol) was dissolved in dry dichloromethane (10 mL), and the solution was cooled to 0° C. Then, TFA (10 mL) was added dropwise and the resulting mixture was stirred at 0° C. for 30 minutes and then at room temperature for 1 h. The reaction was concentrated under reduced pressure, redissolved in toluene and concentrated again. The resulting amine was placed under vacuum for 20 minutes and dissolved in dry DMF (3 mL). DIEA (360 µL, 2.6 mmol) and 6-(dimethylamino)-2,3-naphthalenedicarboylic anhydride were added, and the mixture was stirred at room temperature for 30 minutes. HOBt/HBTU (2 mL 0.2 M solution in DMF) were added and the reaction was stirred at room temperature for 12 h. HOBt/HBTU (1 mL 0.2 M solution in DMF, 0.5 eq.) was added and the reaction mixture was allowed to stir for another 1 hour. The crude reaction was added to 150 mL 2% aqueous NaHCO$_3$ and extracted with EtOAc (3×30 mL). The combined organic layers were dried with Na$_2$SO$_4$ and concentrated under reduced pressure. The residue was loaded in 20% EtOAc/toluene onto a silica column and purified (gradient 20 to 50% EtOAc/hexahes) to afford Fmoc-Dap(6DMN)-O-Allyl as a bright yellow oil (220 mg, >95% yield, R$_f$=0.8 10% MeOH/CH$_2$Cl$_2$). $^1$H-NMR (400 MHz, CDCl$_3$, δ): 3.12 (s, 6H), 4.1-4.4 (m, 5H), 4.65-4.83 (m, 3H), 5.26 (d, 1H, J=10.3 Hz), 5.38 (d, 1H, J=17.1 Hz), 5.9-6.1 (m, 1H), 7.20 (dd, 1H, J$_1$=2.0 Hz, J$_2$=9.1 Hz), 7.29 (c, 2H, J=7.4 Hz), 7.29 (td, 2H, J$_1$=1.7 Hz, J$_2$=5.2 Hz), 7.57 (d, 1H, J=7.6 Hz), 7.60 (d, 1H, J=7.5 Hz), 7.73 (d, 2H, J=7.5 Hz), 7.80 (d, 1H, J=9.1 Hz), 8.03 (s, 1H), 8.10 (s, 1H). $^{13}$C-NMR (100 MHz, CDCl$_3$, δ): 169.9, 168.6, 168.5, 156.0, 150.5, 144.1, 143.8, 141.3, 137.7, 131.5, 128.2, 127.7, 127.4, 127.2, 125.2, 125.5, 123.1, 122.5, 120.0, 119.3, 117.9, 107.9, 67.5, 66.8, 53.8, 47.1, 40.4, 39.2. HRMS-ESI (m/z): [M+H$^+$] calcd for C$_{35}$H$_{31}$N$_3$O$_6$ 590.2291, found, 590.2270.

Fmoc-Dap(6DMN)—O-allyl (226 mg, 0.383 mmol) was dissolved in dry CH$_2$Cl$_2$ (12 mL). Phenyl silane (1.2 mL, 9.6 mmol) and Pd(PPh$_3$)$_4$ (20 mg, 0.014 mmol) were added and the reaction mixture was stirred at room temperature for 30 minutes. The reaction mixture was then directly loaded onto a silica flash column and the desired product purified (gradient, 3% to 5% MeOH/CH$_2$Cl$_2$). Fmoc-Dap(6DMN) was isolated as a yellow solid (210 mg, >95%, R$_f$=0.4 10% MeOH/CH$_2$Cl$_2$). MS-ESI: m/z: 550.1 (MH$^+$), 572 (MNa$^+$), 1099.3 (M$_2$H$^+$). HRMS-ESI (m/z): [M+H$^+$] calcd for C$_{32}$H$_{27}$N$_3$O$_6$ 550.1973, found, 550.1982.

6DMN-GlyOMe:

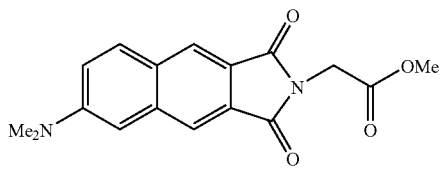

Glycine methyl ester hydrochloride (21 mg, 0.164 mmol) was dissolved in DMF (2 mL), and DIEA (450 µL, 3.28 mmol, 10 eq.) and 6-(dimethylamino)-2,3-naphthalenedicarboylic anhydride (80 mg, 0.328 mmol) were added. The resulting mixture was stirred at room temperature for 10 minutes. HOBt/HBTU (1 mL, 0.2 M in DMF) was added and the reaction mixture was stirred for 12 h. Then for an additional 0.5 mL of the HOBt/HBTU mixture were added, and the reaction was stirred for another hour. The reaction was poured over 100 mL 1% aqueous HCl and extracted with EtOAc (2×50 mL). The combined organic layers were dried with Na$_2$SO$_4$ and concentrated under reduced pressure. The solid residue was purified by flash column chromatography (EtOAc/hexanes 35%) to afford 6DMN-GlyOMe as a bright yellow solid in quantitative yield (R$_f$=0.5 40% EtOAc/hexanes). $^1$H-NMR (400 MHz, CDCl$_3$, δ): 3.12 (s, 6H), 3.76 (s, 3H), 4.47 (s, 2H), 6.96 (d, 1H, J=2.0 Hz), 7.21 (dd, 1H, J$_1$=9.1 Hz, J$_2$=2.5 Hz), 7.81 (d, 1H, J=9.1 Hz), 8.06 (s, 1H), 8.13 (s, 1H). $^{13}$C-NMR (100 MHz, CDCl$_3$, δ): 168.1, 167.9, 167.8, 150.6, 137.8, 131.4, 128.5, 127.5, 125.2, 123, 1, 122.8, 117.9, 107.9, 52.8, 40.4, 38.9. HRMS-ESI (m/z): [M+H$^+$] calcd for C$_{17}$H$_{16}$N$_2$O$_4$ 313.1188, found, 313.1201. UV: δ (388 nm, M$^-$cm$^{-1}$)=7980.

Peptide Synthesis:

Peptide synthesis was carried using standard Fmoc-based solid phase peptide synthesis (SPPS) protocols on a 0.05 to 0.1 mmol scale using a 0.21 mmol/g loading PAL-PEG-PS solid support. Amino acids were coupled in three-fold excess using a mixture of 0.2 M HBTU/0.2 M HOBt in DMF as activating agents. Each amino acid was activated for two minutes with the HBTU/HOBt mixture (1 eq.) and diisopropylethylamine (DIPEA), 0.195 M in DMF (1.5 eq.) before being added to the resin. Peptide coupling was monitored using the 2,4,6-trinitrobenzenesulphonic acid (TNBS) test. (Hancock, W. S.; Battersby, J. E. *Anal. Biochem.* 1976, 71, 260-264) Amino acids were used as protected Fmoc-amino acids with the standard side chain protecting groups: Fmoc-Ala-OH, Fmoc-Arg(Pbf)-OH, Fmoc-Asp(OtBu)-OH, Fmoc-Glu(OtBu)-OH, Fmoc-Ile-OH, Fmoc-Ser(tBu)-OH, Fmoc-Thr(tBu)-OH, Fmoc-Tyr(tBu)-OH, Fmoc-Val-OH and Fmoc-Dap(6DMN). Phosphotyrosine was introduced as the monobenzyl ester Fmoc-Tyr(PO(OBzl)OH)-OH. High-performance liquid chromatography (HPLC) was performed using a Waters 600E HPLC fitted with a Waters 600 automated control module and a Waters 2487 dual wavelength absorbance detector recording at 228 and 280 nm. For analytical HPLC a Beckman Ultrasphere C$_{18}$, 5 µm, 4.6×150 mm reverse-phase column was used. For preparative separations a YMC-pack, C$_{18}$, 250×20 mm reversed phase column was used. The standard gradient for analytical and preparative HPLC used was 93:7 to 5:95 over 35 minutes (water:acetonitrile, 0.1% TFA). The 6DMN side chain proved resistant to the standard mildly basic amino acid coupling conditions (0.12 M diisopropylethylamine), the Fmoc deprotection conditions (20% piperidine), and the acidic resin cleavage and deprotection cocktail (95% TFA).

Quantum Yield Measurements:

Quantum yields (Φ) were measured by comparison with a standard, which emits in a similar region to the test sample. From the available standard compounds quinine sulfate in 0.1 M H$_2$SO$_4$ (Φ=0.54) was selected. (Melhuish, W. B. *J. Phys. Chem.*, 1961, 65, 229-235) Absorbance of the measured solutions did not exceed 0.1 at and above the excitation wavelength to avoid non-linear effects.

UV absorbance at the excitation wavelength (375 nm), and fluorescence emission spectra of a series of solutions of the standard and compound were recorded. Solutions were prepared with different absorbances, ranging from 0 (solvent blank) to 0.1. A series of graphs of integrated fluorescence vs. absorbance were obtained. The data were fitted to a linear equation with gradient (grad), and intercept=0. See FIG. 5 as an example of the plots obtained.

Figure 5:
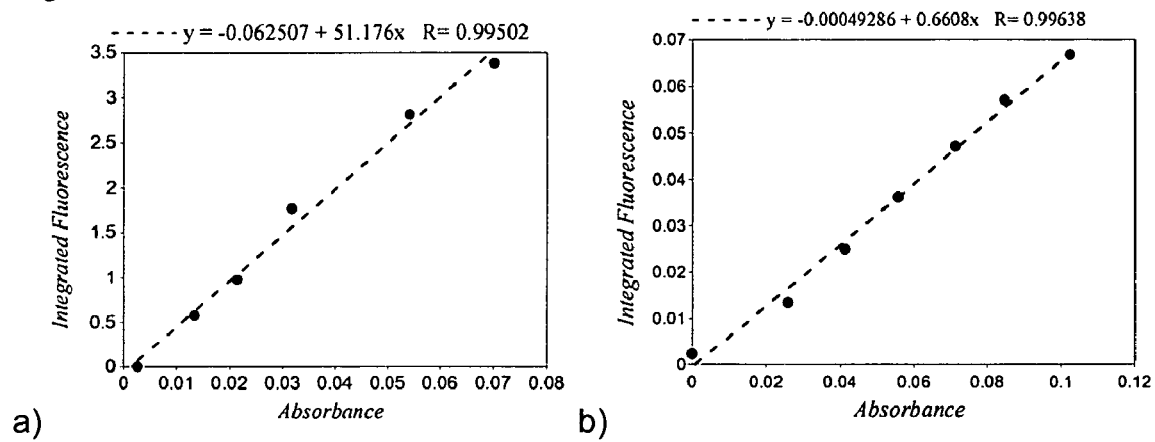
FIG. 5 are plots of integrated fluorescence vs. absorbance used to calculate the quantum yield ($\Phi$) of Ac-Gly-Dap (6DMN)-Gln-pTyr-Glu-Asn-Val-Gln-Ser-(CONH$_2$) (SEQ ID NO: 6). The quantum yield is proportional to the gradient of the plot. The absolute value is calculated using a standard sample, quinine sulfate. a) Integrated fluorescence vs. absorbance for standard solution: quinine sulfate in 0.1 M H$_2$SO$_4$. b) Integrated fluorescence vs. absorbance for test solution: Ac-Gly-Dap(6DMN)-Gln-pTyr-Glu-Asn-Val-Gln-Ser-(CONH$_2$) (SEQ ID NO: 6) in 10 mM phosphate buffer, pH 7.5.

The gradients of graphs in FIG. 5 are proportional to the quantum yield of the different samples. Absolute values were calculated using the standard sample, which has a fixed and known fluorescence quantum yield value, according to the following equation:

$$\Phi_x = \Phi_{std}\left(\frac{grad_x}{grad_{std}}\right)\left(\frac{\eta_x^2}{\eta_{std}^2}\right) \quad (1)$$

Where the subscripts std and x denote standard and test respectively. The value $\Phi$ is the fluorescence quantum yield, grad is the gradient (grad) from the plot of integrated fluorescence intensity vs. absorbance, and $\eta$ the refractive index of the solvent.

Quantum Yield of Compound (VIII) 6DMN-GlyOMe

Figure 6:
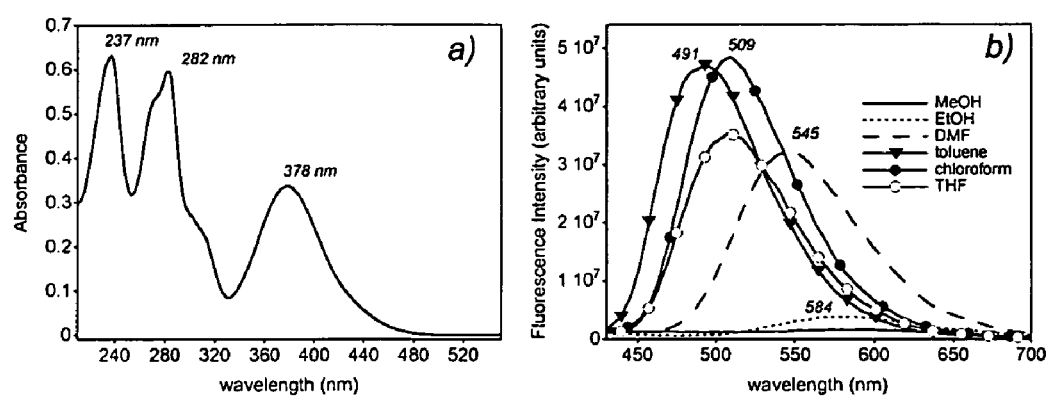
FIG. 6 are UV absorption and fluorescence emission spectra of compound VIII, 6DMN-GlyOMe. a) UV absorption spectra (40 μM) in methanol. b) Fluorescence emission spectra in different solvents. Labels show maximum emission wavelengths for selected solvents (toluene, chloroform and methanol).

The UV absorbance spectra (40 µM in methanol) and fluorescence emission spectra of compound (VIII), 6DMN-GlyOMe are shown in FIG. 6 and tabulated in Table 4. The UV spectrum of 6DMN-GlyOMe has an intense absorption band at 378 nm which is not found in unsubstituted 2,3-naphthalimides. The maximum excitation wavelength of 6DMN-GlyOMe is at 375 nm.

TABLE 4

Photophysical Properties of 6DMN-GlyOMe in Different Solvents:

| solvent | absorbance maximum (nm) | emission maximum (nm) | quantum yield $(\Phi)^b$ |
|---|---|---|---|
| water[a] | 388 | 592 | 0.002 |
| methanol | 382 | 589 | 0.012 |
| 2-propanol | 385 | 589 | 0.018 |
| ethanol | 379 | 584 | 0.027 |
| acetonitrile | 380 | 549 | 0.135 |
| DMF | 380 | 545 | 0.155 |
| acetone | 375 | 532 | 0.148 |
| tetrahydrofuran | 373 | 510 | 0.147 |
| 1,4-dioxane | 372 | 498 | 0.220 |
| dichloromethane | 379 | 517 | 0.210 |
| chloroform | 380 | 509 | 0.225 |
| toluene | 373 | 491 | 0.208 |

[a]Because of solubility limitations, the quantum yield in water was calculated using peptide Abl-bp.
[b]Quantum yields ($\Phi$) were measured in comparison to quinine sulfate in 0.1 M $H_2SO_4$ ($\Phi$ = 0.54) as the standard.

Quantum yields ($\Phi$) were measured in the solvents listed in Table 2 by comparison with a standard, which emits in a similar region to 6DMN-GlyOMe. Quinine sulfate in 0.1 M $H_2SO_4$ ($\Phi$=0.54) was used as the standard. (Melhuish, W. B. *J. Phys. Chem.*, 1961, 65, 229-235). Solutions were prepared at different concentrations such that the absorbance measurements ranged between 0 and 0.1 at and above the excitation wavelength to avoid non-linear effects.

UV absorbance at the excitation wavelength (375 nm), and fluorescence emission spectra of a series of solutions of the standard and 6DMN-GlyOMe were recorded. A series of graphs of integrated fluorescence vs. absorbance were obtained. The data were fitted to a linear equation with gradient (grad), and intercept=0. The gradient (grad) is proportional to the quantum yield of the sample. Absolute values were calculated using the standard sample, which has a fixed and known fluorescence quantum yield value, according to the equation above.

Lippert-Mataga Plots for Compound VIII

It is known that the solvent sensitivity to polarity can be analyzed in terms of difference in the dipole moments in the ground and the excited state and it has been found that the most sensitive fluorophores are those with the largest changes in the dipole moment. This can be estimated from a Lippert-Mataga plot, which is essentially a plot of the Stokes shift of the fluorescence emission versus the solvent polarity. (Lippert, V. E. *Z. Elektrochem.* 1957, 61, 962-975; Mataga, N.; Kaifu, Y.; Koizumi, M. *Bull. Chem. Soc. Jpn.* 1956, 29, 465-470.)

Figure 7:
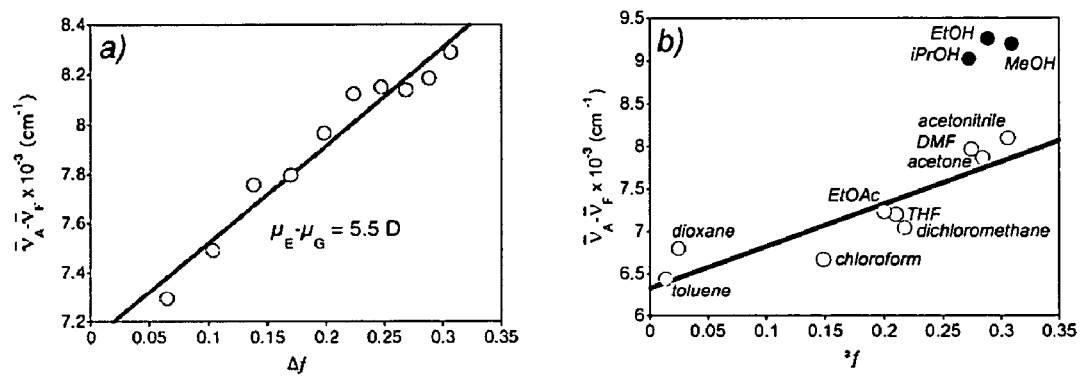
FIG. 7 are Lippert-Mataga plots for compound VIII, 6DMN-GlyOMe. (a) Plot of $\bar{v}_A-\bar{v}_F$ (Stokes shift) vs. $\Delta f$ (orientation polarizability of the solvent) for 6DMN-GlyOMe in a series of 1,4-dioxane/acetonitrile mixtures. $\bar{v}_A-\bar{v}_F$ ($\Delta\bar{v}$) is the difference in the maximum absorption and emission wavelengths, expressed in wavenumbers. $\bar{v}_A-\bar{v}_F$ ($\Delta\bar{v}$) was measured from a series of 1,4-dioxane/acetonitrile mixtures. $\Delta f$ was calculated based upon the composition of the 1,4-dioxane/acetonitrile mixture using the dielectric constant and refraction index of 1,4-dioxane and acetonitrile. The slope corresponds to $\mu_e-\mu_g$ ($\Delta\mu$) which is the difference between the dipole moments of the excited and ground states for 6DMN-GlyOMe. The greater the change in the dipole moment, the more sensitive the fluorophore. (b) Plot of $\bar{v}_A-\bar{v}_F$ (Stokes shift) vs. $\Delta f$ (orientation polarizability of the solvent) for 6DMN-GlyOMe in a series of different solvents. $\Delta f$ was calculated for each solvent using the dielectric constant and refraction index of the corresponding solvent. The line corresponds to the best linear fit to the data, excluding the values obtained for protic solvents (methanol, isopropanol and ethanol, closed circles), indicating that the Stokes shift is proportional to the orientation polarizability. Protic solvents (methanol, isopropanol and ethanol) show disproportionately large Stokes shifts which may be due to two different excited states. (Kosower, E. M.; Dodiuk, H. *J. Am. Chem. Soc.* 1974, 96, 6195-6196; Kosower, E. M. *Acc. Chem. Res.* 1982, 15, 259-266; Saha, S.; Samanta, A. *J. Phys. Chem. A* 2002, 106, 4763-4771)

The difference ($\Delta\bar{v}$) in the maximum absorption ($\bar{v}_A$) and emission wavelengths ($\bar{v}_F$), known as the Stokes shift and expressed in wavenumbers, is plotted vs. $\Delta f$. The term $\Delta f$ is called the orientation polarizability and can be calculated according to the following equation:

$$\Delta f = \left(\frac{\varepsilon - 1}{2\varepsilon + 1} - \frac{n^2 - 1}{2n^2 + 1}\right) \quad (2)$$

where $\varepsilon$ is the solvent dielectric constant and n is the solvent refraction index. The plot of ($\Delta\bar{v}$) for compound (VIII) vs. $\Delta f$ for the solvents listed in Table 2 is shown in FIG. 7(*b*).

The term $\Delta f$ can also be calculated for a mixture of solvents. FIG. 7(*a*) shows the plot of ($\Delta\bar{v}$) for compound (VIII) vs. $\Delta f$ for a series of 1,4-dioxane/acetonitrile mixtures. In this case, $\Delta f$ is obtained for each mixture using $\varepsilon$ and n values calculated using the molar fractions ($\chi$) in the equation as follow:

$$\varepsilon = (\chi_{acetonitrile})(38.8) + (\chi_{diox})(2.218) \quad (3)$$

$$n = (\chi_{acetonitrile})(1.3442) + (\chi_{diox})(1.4224) \quad (4)$$

where $\chi_{acetonitrile} + \chi_{diox} = 1$.

The relationship between $\Delta\bar{v}$ and $\Delta f$ is expressed by the following equation:

$$\begin{aligned}\bar{v}_A - \bar{v}_F &= \Delta\bar{v} \\ &= \frac{2}{hca_0^3}\left(\frac{\varepsilon - 1}{2\varepsilon + 1} - \frac{n^2 - 1}{2n^2 + 1}\right)(\mu_e - \mu_g)^2 \\ &= \frac{2\Delta f}{hca_0^3}\Delta\mu^2\end{aligned} \quad (5)$$

where c is the velocity of light, h is Plank's constant, $\mu_e - \mu_g$ is the difference between the dipole moments of the excited and the ground states respectively ($\Delta\mu$), and $a_0$ is the radius of the Onsager cavity around the compound. The Onsager radius for compound VIII was calculated from the optimized structure obtained with a DFT minimization using the Gaussian program (Pople, J. A. et al. *Gaussian* 98 (Gaussian, Inc., Pittsburgh, Pa., 1998), (B3LYP functional using 6-31G(d) orbital base). The Onsager radius (4.19 Å) was taken as half of the average distance between nitrogen of the amine donor and the two carbonyl oxygens, which corresponds to the longest distance across the molecule where charge separation can take place. (Mukherjee, S., Chattopdhyay, A., Samanta, A., Soujanya, T. *J. Phys. Chem.* 1994, 98, 2809-2812.) As can be seen in FIG. 7(*a*), the Stokes shift of compound VIII in a series of mixtures of 1,4-dioxane/acetonitrile changes linearly in response to the solvent polarity, which correlates with an increase in the dipole moment ($\Delta\bar{v}$) of 5.5 D.

Lippert plots also give evidence of specific solvent effects for protic solvents. As can be seen in FIG. 7(*b*), in most solvents the Stokes shift is proportional to the orientation polarizability. However, protic solvents induce a disproportionately large Stokes shift. This phenomenon has also been observed for other environment-sensitive fluorophores, and has been explained as the result of emission from two different excited states: one with higher dipole moment that is stabilized in polar environments, and another less polar excited state responsible for the emission in less polar media. (Kosower, E. M., Dodiuk, H. *J. Am. Chem. Soc.* 1974, 96, 6195-6196; Kosower, E. M. *Acc. Chem. Res.* 1982, 15, 259-266; Saha, S., Samanta, A. *J. Phys. Chem. A* 2002, 106, 4763-4771.)

Fluorescence Titrations and Determination of Binding Constant, $K_d$:

Peptide stock solutions of known concentration (determined by UV absorbance at 388 nm, E=7980 M−1 cm−1) were used to prepare 5 μM peptide concentration samples in buffered water (150 μL total volume, 100 mM NaCl, 10 mM sodium phosphate, pH 7.5). 2 μL aliquots of the corresponding stock protein solution (GST-Crk SH2, GST-Abl SH2 or GST-PI3K SH2, concentration determined by Bio-Rad Protein Assay) were consecutively added, and fluorescence emission spectra were recorded 1 minute after each addition (excitation 395 nm, 2 nm excitation and emission slit width). The increase in emission intensity at the maximum emission wavelength was plotted against total protein concentration and fitted by least-square analysis assuming a 1 to 1 binding mode to obtain the apparent Kd.

Expression of GST-Crk SH2:

Human Crk SH2 domain was expressed as a GST fusion protein transformed into *E. coli* NB42 strain. Expression of SH2 domains was carried out following reported conditions. The culture was inoculated intro prewarmed LB media with carbenicilin 50 μg/mL. The sample was shaken at 37° C. for at least 2 h (passed semi-logarithmic growth $A_{600}$=0.5)). IPTG was added to 0.1 mM; (4) the sample was shaken at 25° C. for four hours. Using lower temperature than previously reported conditions minimizes inclusion bodies formation. The sample was then centrifuged (5000 g for 30 min at 4° C.) and the pellet was resuspended in ice-cold lysis buffer (see below). The slurry was then sonicated until cells were disrupted (20 sec sonication and 30 seconds in ice for 4 times). Note: it was observed that treatment of the resuspended bacteria with lysozyme (1 mg/mL) for 30 min at 4° C. improved the lysis process and resulted in higher yields.

Lysis buffer PBS with 100 mM EDTA, 1% Triton X-100, 10% glycerol, 1 mM DTT, AEBSF, leupeptin and PepA. (add 100 μL AEBSF+25 μL Leupeptin+12.5 μL Pep A+ to 10 mL total buffer).

Purification: The sample was recentrifuged to remove particulate debris (5000 g for 30 min at 4° C.). Then the supernatant was incubated for at least 1 hour with 10 mL of glutathione Sepharose 4 Fast Flow (Amersham Biosciences). The column was equilibrated with 5 volumes of binding buffer at 4° C. The sample was the loaded using a syringe and low flow rate (0.2 to 0.5 mL/min) at 4° C. The column was then washed with 5 volumes of binding buffer (higher rate of 1 mL/min) room temperature. The GST fusion protein was eluted with elution buffer at room temperature. The pooled fractions were then collected and analyzed using gel electrophoresis to confirm purity using 10% SDS-PAGE. Binding buffer: PBS pH 7.4 (140 mM NaCl, 2.7 mM KCl, 10 mM $Na_2HPO_4$, 1.8 mM $NaHPO_4$). Elution buffer: 50 mM Tris-HCl, 10 mM reduced glutathione, pH 8.

Western Blot:

The gel was transferred to a nitrocellulose membrane (1 h, 100 V), and probed using the standard procedure: blocked overnight with TBST+powder milk; washed with TBST (2×10 mL×10 min.); incubated with primary antibody (anti-GST, dilution 1:10,000 in TBST) for 30 min; washed with TBST (3×10 mL×10 min.); incubated for 30 min with secondary antibody (anti-goat conjugated with alkaline phosphatase, 1:1,000 dilution in TBS); washed with TBST (2×10 mL×10 min.); washed with TBS (1×10 mL×10 min.); One Step NBT/BCIP added and incubated until the bands appeared; then quenched the reaction with $ddH_2O$. Once the protein was isolated, it was separated from the reduced glutathione using the Ultrafree-15 centrifugal filter (Biomax-5). The stock solution of Crk-SH2-GST was concentrated at 2000 g until the volume was approximately 2 mL. Phosphate buffer (10 mM phosphate, pH 7.5 100 mM NaCl) was added to a final volume of 15 mL and centrifuged again to a final volume of 2 mL. This procedure was repeated three times to ensure that the concentration of the contaminant solutes was minimal. The final volume was 1.2 mL.

Bio-Rad Protein Assay was used to quantify the isolated following the standard procedure. Dye reagent was prepared by diluting 1 part Dye Reagent Concentrate with 4 parts distilled water. Stock BSA dilutions were prepared corresponding to 0.1, 0.2, 0.3, 0.4, 0.5 0.6, 0.7, 0.8 and 0.9 mg/mL as follows. 20 μL of each stock dilution were added to 980 μL dye reagent and incubated at room temperature for 5 min. The absorbance was measured at 595 nm using a blank of 20 μL of distilled water and 980 μL dye reagent prepared at the same time as the samples. The observed absorbance was plotted against BSA concentration.

Three samples of increasing concentration of Crk-SH2-GST stock solution were prepared. Then, 10, 15 and 20 μL of stock solution with water up to 20 μL as necessary were added to 980 μL dye reagent. Absorbance measurements of these solutions in comparison with the standard curve afforded a final concentration of 11 mg/mL of Crk-SH2-GST.

Expression of GST-AbI SH2, GST-Src SH2 and GST-PI3K SH2:

Abl-SH2 was received as a GST fusion in a pGEX-KT vector, amp-resistant, IPTG-inducible. The SH2 domain was cloned using BamH1 (5') EcoR1 (3') sites.

The expression of GST-Abl SH2 GST-Src SH2 and GST-PI3K SH2 was carried out using the same protocol and conditions as the GST-Crk SH2 mutant, but in these cases it was found that expression at 37° C. resulted in increased yields of protein with no inclusion bodies formation.

Src and PI3K SH2 domains were expressed and purified as GST fusion following reported procedures. (Smith, D. B.; Johnson, K. S. Gene, 1988, 67, 31-40) In short, plasmids including GST-fusion proteins were transformed into bacteria (*E. coli* DH5α chemically competent cells, Invitrogen). Bacteria were grown to mid log phase, induced at 37° C. for 3-4 hours with isopropyl-1-thio-β-D-galactopyranoside, and lysed by treatment with lysozyme (1 mg/mL, 30 minutes) followed by sonication (PBS buffer pH 7.4 with 100 mM EDTA, 1% Triton X-100, 10% glycerol, 1 mM DTT, 0.1 mM AEBSF, 30 μg/mL Leupeptin and 0.5 μg/mL Pepstatin A). The lysates were clarified by centrifugation, and fusion proteins were purified by binding to glutathione-agarose beads (Amersham Biosciences). Proteins were eluted from the beads (50 mM Tris-HCl, 10 mM reduced glutathione, pH 8), and finally concentrated by centrifugation through a cellulose membrane with a 10,000 Da cutoff (Millipore). Proteins were quantified using the Micro BCA protein Assay Kit (Pierce) relative to a BSA standard. All fusion proteins were analyzed by Coomasie staining and Western analysis with anti-GST antibodies.

The invention claimed is:

1. A compound of formula (I):

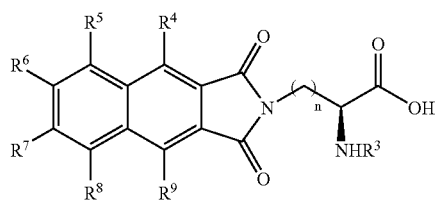

(I)

where $R^4$, $R^5$, $R^6$, $R^7$, $R^8$, and $R^9$ are each independently hydrogen, fluorine, or alkyl, where one of $R^6$ or $R^7$ is —$NR^1R^2$;

$R^1$ and $R^2$ are each independently hydrogen or alkyl; or $R^1$ and $R^2$ together with the nitrogen to which they are attached, may form a substituted or unsubstituted 5- or 6-membered ring; wherein said nitrogen is not conjugated with said 5- or 6-membered ring;

$R^3$ is hydrogen or a N-protecting group;

n is 1, 2, 3 or 4.

2. The compound of claim 1, which is of the formula (II):

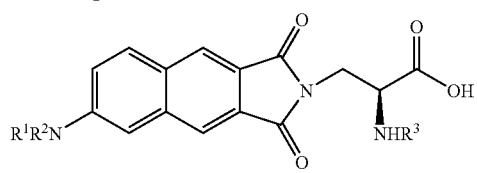

(II)

where $R^1$ and $R^2$ are each independently hydrogen or alkyl; or $R^1$ and $R^2$ together with the nitrogen to which they are attached, may form a substituted or unsubstituted 5- or 6-membered ring; wherein said nitrogen is not conjugated with said 5- or 6-membered ring; and $R^3$ is hydrogen or a N-protecting group.

3. The compound of claim 2, where $R^2$ is alkyl.

4. The compound of claim 1, which is of the formula (III):

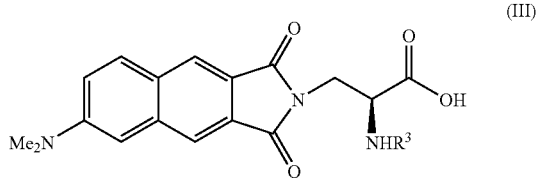

(III)

where $R^3$ is hydrogen or a N-protecting group.

* * * * *

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial
<220> FEATURE:
<223> OTHER INFORMATION: peptide containing SH2 domain
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: Dap(6DMN)
<220> FEATURE:
<221> NAME/KEY: MOD_RES
<222> LOCATION: (3)..(3)
<223> OTHER INFORMATION: PHOSPHORYLATION

<400> SEQUENCE: 1

Glu Gln Tyr Asp His Pro Asn Ile
1               5

<210> SEQ ID NO 2
<211> LENGTH: 8
<212> TYPE: PRT
<213> ORGANISM: Artificial
<220> FEATURE:
<223> OTHER INFORMATION: peptide containing SH2 domain
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: Dap(6DMN)
<220> FEATURE:
<221> NAME/KEY: MOD_RES
<222> LOCATION: (3)..(3)
<223> OTHER INFORMATION: PHOSPHORYLATION

<400> SEQUENCE: 2

Glu Gly Tyr Asp His Pro Asn Ile
1               5

<210> SEQ ID NO 3
<211> LENGTH: 8
<212> TYPE: PRT
<213> ORGANISM: Artificial
<220> FEATURE:
<223> OTHER INFORMATION: peptide containing SH2 domain
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: Dap(6DMN)
<220> FEATURE:
<221> NAME/KEY: MOD_RES
<222> LOCATION: (3)..(3)
<223> OTHER INFORMATION: PHOSPHORYLATION

<400> SEQUENCE: 3

Glu Gly Tyr Glu Asn Val Gln Ser
1               5
```

```
<210> SEQ ID NO 4
<211> LENGTH: 7
<212> TYPE: PRT
<213> ORGANISM: Artificial
<220> FEATURE:
<223> OTHER INFORMATION: peptide containing SH2 domain
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: Dap(6DMN)
<220> FEATURE:
<221> NAME/KEY: MOD_RES
<222> LOCATION: (2)..(2)
<223> OTHER INFORMATION: PHOSPHORYLATION

<400> SEQUENCE: 4

Glu Tyr Glu Asn Val Gln Ser
1               5

<210> SEQ ID NO 5
<211> LENGTH: 8
<212> TYPE: PRT
<213> ORGANISM: Artificial
<220> FEATURE:
<223> OTHER INFORMATION: peptide containing Dap(6DMN)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: Dap(6DMN)
<220> FEATURE:
<221> NAME/KEY: MOD_RES
<222> LOCATION: (3)..(3)
<223> OTHER INFORMATION: PHOSPHORYLATION

<400> SEQUENCE: 5

Gly Gln Tyr Asp His Pro Asn Ile
1               5

<210> SEQ ID NO 6
<211> LENGTH: 8
<212> TYPE: PRT
<213> ORGANISM: Artificial
<220> FEATURE:
<223> OTHER INFORMATION: peptide containing Dap(6DMN)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: Dap(6DMN)
<220> FEATURE:
<221> NAME/KEY: MOD_RES
<222> LOCATION: (3)..(3)
<223> OTHER INFORMATION: PHOSPHORYLATION

<400> SEQUENCE: 6

Gly Gln Tyr Glu Asn Val Gln Ser
1               5

<210> SEQ ID NO 7
<211> LENGTH: 7
<212> TYPE: PRT
```

```
<213> ORGANISM: Artificial
<220> FEATURE:
<223> OTHER INFORMATION: peptide containing Dap(6DMN)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Dap(6DMN)
<220> FEATURE:
<221> NAME/KEY: MOD_RES
<222> LOCATION: (2)..(2)
<223> OTHER INFORMATION: PHOSPHORYLATION

<400> SEQUENCE: 7

Gln Tyr Glu Asn Val Gln Ser
1               5
```